(12) United States Patent
Bredehoft et al.

(10) Patent No.: US 11,857,267 B2
(45) Date of Patent: Jan. 2, 2024

(54) SYSTEM AND METHOD FOR NAVIGATION

(71) Applicant: Medtronic Navigation, Inc., Louisville, CO (US)

(72) Inventors: Leo Bredehoft, Longmont, CO (US); Brad Jacobsen, Erie, CO (US); Shai Ronen, Louisville, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 191 days.

(21) Appl. No.: 16/855,573

(22) Filed: Apr. 22, 2020

(65) Prior Publication Data

US 2021/0330392 A1 Oct. 28, 2021

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 2034/2051* (2016.02); *A61B 2034/2055* (2016.02); *A61B 2560/0223* (2013.01)

(58) Field of Classification Search
CPC . A61B 34/20; A61B 90/37; A61B 2034/2051; A61B 2034/2055; A61B 2034/0223
See application file for complete search history.

(56) References Cited

U.S. PATENT DOCUMENTS

| | | | |
|---|---|---|---|
| 4,039,749 A | 8/1977 | Gordy et al. | |
| 4,203,070 A * | 5/1980 | Bowles | H04B 1/69 375/317 |
| 4,653,069 A | 3/1987 | Roeder | |
| 5,592,939 A | 1/1997 | Martinelli | |
| 5,913,820 A | 6/1999 | Bladen et al. | |
| 5,983,126 A | 11/1999 | Wittkampf | |
| 6,474,341 B1 | 11/2002 | Hunter et al. | |
| 6,940,941 B2 | 9/2005 | Gregerson et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 8,150,494 B2 | 4/2012 | Simon et al. | |
| 8,175,681 B2 | 5/2012 | Hartmann et al. | |
| 8,503,745 B2 | 8/2013 | Simon et al. | |
| 8,737,708 B2 | 5/2014 | Hartmann et al. | |
| 9,737,235 B2 | 8/2017 | Hartmann | |

(Continued)

FOREIGN PATENT DOCUMENTS

| | | | |
|---|---|---|---|
| DE | 102010013499 A1 * | 10/2011 | ............. A61B 34/20 |
| EP | 3552545 A1 | 10/2019 | |
| WO | 2006094156 A2 | 9/2006 | |

OTHER PUBLICATIONS

Machine Translation of DE102010013499A1 (Year: 2011).*

(Continued)

*Primary Examiner* — John Denny Li
(74) *Attorney, Agent, or Firm* — Harness, Dickey & Pierce, P.L.C.

(57) ABSTRACT

Disclosed is a system for assisting in guiding and performing a procedure on a subject. The subject may be any appropriate subject such as inanimate object and/or an animate object. The guide and system may include various manipulable or movable members, such as robotic systems, and may be registered to selected coordinate systems.

16 Claims, 9 Drawing Sheets

(56) References Cited

U.S. PATENT DOCUMENTS

| | | | |
|---|---|---|---|
| 11,571,261 B2 | 2/2023 | Bredehoft et al. | |
| 2003/0184285 A1* | 10/2003 | Anderson | A61B 34/20 606/1 |
| 2004/0143183 A1* | 7/2004 | Toyoda | A61B 5/062 128/899 |
| 2004/0199072 A1 | 10/2004 | Sprouse et al. | |
| 2008/0132909 A1 | 6/2008 | Jascob et al. | |
| 2009/0209852 A1 | 8/2009 | Mate et al. | |
| 2009/0299174 A1 | 12/2009 | Wright et al. | |
| 2010/0158331 A1 | 6/2010 | Jacobs et al. | |
| 2014/0258800 A1* | 9/2014 | Gilbert | A61B 18/1206 714/736 |
| 2014/0329562 A1* | 11/2014 | Lea | H01Q 25/00 455/562.1 |
| 2015/0201864 A1* | 7/2015 | Govari | A61B 5/062 600/409 |
| 2016/0135903 A1* | 5/2016 | Christian | G06T 7/73 382/103 |
| 2018/0116729 A1* | 5/2018 | Morgan | A61B 1/00158 |
| 2018/0172784 A1 | 6/2018 | Brunner et al. | |
| 2019/0000560 A1 | 1/2019 | Berman et al. | |
| 2019/0104994 A1 | 4/2019 | Valdastri et al. | |
| 2019/0226826 A1 | 7/2019 | Schneider et al. | |
| 2019/0328272 A1 | 10/2019 | Ronen et al. | |
| 2021/0330391 A1 | 10/2021 | Bredehoft et al. | |

OTHER PUBLICATIONS

International Search Report and Written Opinion regarding International Application No. PCT/US2021/028412, dated Jul. 28, 2021.
Invitation to Pay Additional Fees regarding International Application No. PCT/US2021/028405, dated Jul. 30, 2021.
International Search Report and Written Opinion regarding International Application No. PCT/US2021/028393, dated Aug. 3, 2021.
Li Mengfei et al.: "A robust electromagnetic tracking system for clinical applications", Conference CURAC 2015, Bremen, Germany, vol. 14, Sep. 17, 2015 (Sep. 17, 2015), XPO55826072, Retrieved from the Internet: URL: https://www.researchgate.net/publication/282245201 A robust electromagnetic_tracking_system_for_clinical_applications [retrieved on Jul. 20, 2021].
International Search Report and Written Opinion regarding International Application No. PCT/US2021/028405, dated Sep. 21, 2021.
International Preliminary Report on Patentability corresponding to PCT/US2021/028405, Written Opinion of the International Searching Authority (EP/ISA), dated Nov. 3, 2022.
Torrieri, D. (2005). Principles of spread-spectrum communication systems (vol. 1). Heidelberg: Springer. , pp. vii-viii (Year: 2005).

* cited by examiner

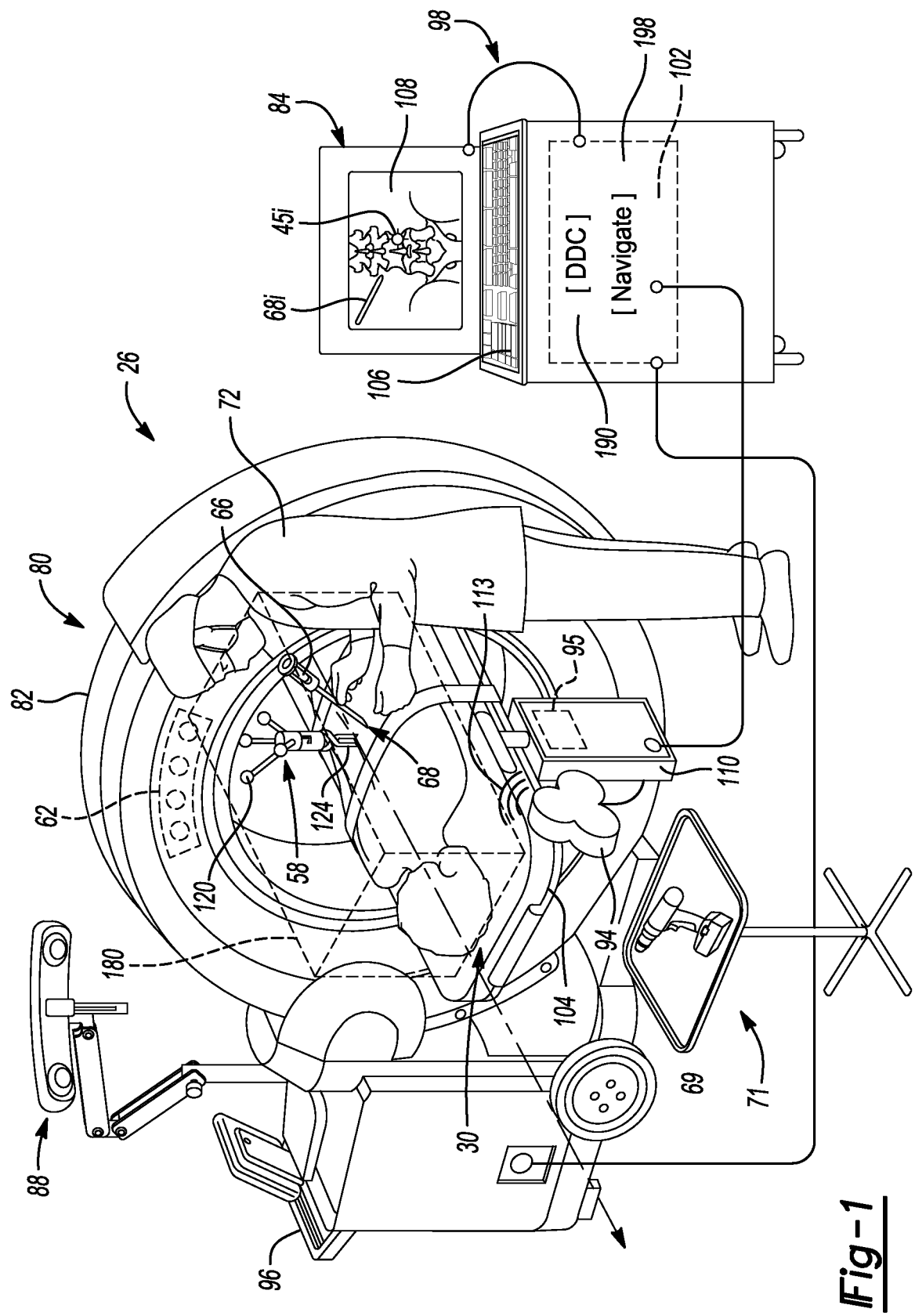

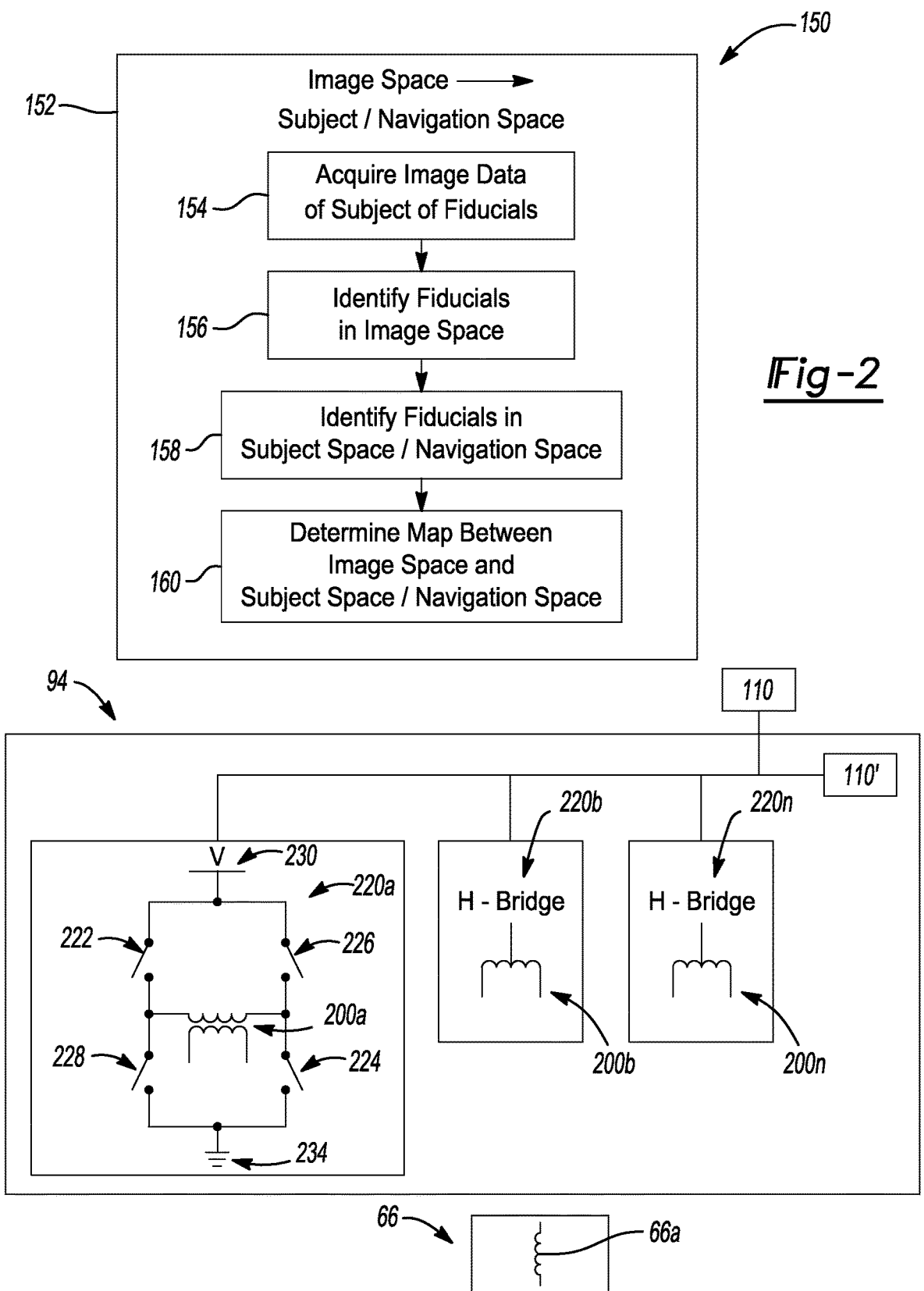

SYSTEM AND METHOD FOR NAVIGATION

CROSS-REFERENCE TO RELATED APPLICATIONS

This application includes subject matter similar to that disclosed in concurrently filed U.S. patent application Ser. No. 16/855,487 filed Apr. 22, 2020 and U.S. patent application Ser. No. 16/855,521 filed Apr. 22, 2020. The entire disclosures of each of the above applications are incorporated herein by reference.

FIELD

The subject disclosure is related to data communication in a navigation system.

BACKGROUND

This section provides background information related to the present disclosure which is not necessarily prior art.

A surgical procedure may be performed on a subject, such as a human subject. The surgical procedure may require an incision into a subject to obtain access to tissue or organs covered by a dermal layer of a subject. Visual access or visual acuity in these areas may be limited due to covering by opaque tissues. Accordingly, determining a pose of an instrument within a subject may be selected.

SUMMARY

This section provides a general summary of the disclosure, and is not a comprehensive disclosure of its full scope or all of its features.

A navigation system may be used to track and determine a pose, which can include at least some coordinates of position and/or orientation, of an instrument over time. In various embodiments, pose of the instrument is understood to include at least some tracked or navigated position coordinates (e.g. x, y, z) and/or orientation coordinates (e.g. roll, pitch, yaw). The navigation system may track a position and/or orientation, including six degree of freedom of motion (e.g. a three-dimensional position and a plurality, e.g. pitch, roll, and yaw orientation). The pose or position and/or orientation of the tracked instrument, therefore, may be determined over time. In various embodiments a visual representation of the instrument may be illustrated with a display device relative to a portion of the subject.

The navigation system, therefore, may be used to determine a position and/or orientation and/or a combination as a pose, including a plurality of positions and/or orientations and/or poses, of the instrument over time. In various embodiments, the pose of the tracked instrument may be determined relative to a subject. The subject may be any appropriate subject such as a living or non-living subject. In various embodiments, a non-living subject may include a hollow or enclosed casing, or other appropriate inanimate object. The inanimate object may have an outer covering that is opaque. Accordingly, a navigation or tracking system may be used to track an instrument during use relative to the inanimate object.

In various embodiments, the subject may include a living subject, such as a human subject. A procedure may include a surgical procedure where an instrument is posed within a subject for a selected period of time to perform a procedure, such as a stent placement, deep brain stimulation probe placement, or placing or implanting other implantable member. Further, selected procedures may include a bone resection, bore formation, or the like relative to the subject. Regardless, the pose of the instrument may be determined with the navigation system.

The navigation system may operate by transmitting data between various elements or portions of the tracking system. For example, in various embodiments, the navigation system may include a tracking device connected with an instrument (e.g. fixed or incorporated into the instrument) that wirelessly transmits a signal to an array. The array may include an antenna array, as discussed further herein. Similarly, or alternatively, the array may transmit a signal wirelessly to be received by the tracking device.

A spread spectrum, which may include various techniques as discussed herein, may be used to transmit a signal, determine a distorted signal and to either disregard and/or correct for the distorted signal. A spread spectrum system, such as frequency hopping, may include modulation and demodulation of a selected signal, and selected transforms of a signal to confirm or eliminate distortion or distorted signals within a system. Thus, the navigation system may incorporate a spread spectrum system to confirm or determine a signal for the tracking device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is diagrammatic view illustrating an overview of a navigation system, according to various embodiments;

FIG. 2 is a flowchart of a method of registration, according to various embodiments;

FIG. 3 is a schematic diagram of a localizer, according to various embodiments, and a tracker, according to various embodiments;

Corresponding reference numerals indicate corresponding parts throughout the several views of the drawings.

DETAILED DESCRIPTION

Figure 4A:
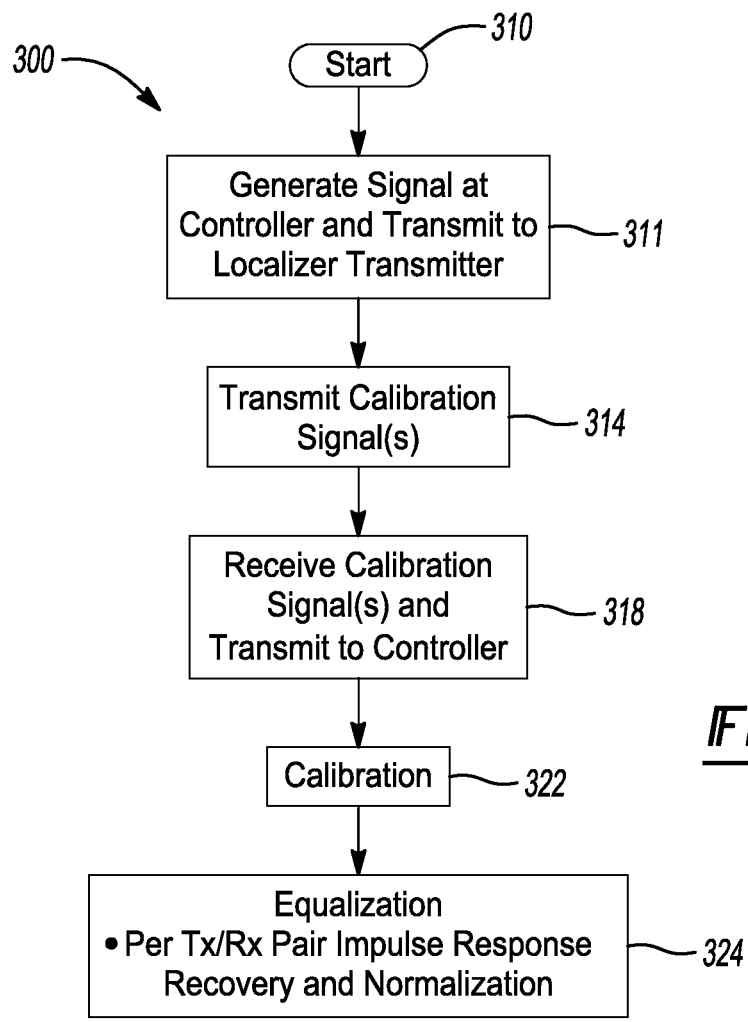
FIG. 4A is a flowchart of a equalization in a spread spectrum navigation system, according to various embodiments.

Example embodiments will now be described more fully with reference to the accompanying drawings.

Disclosed herein are exemplary embodiments, as discussed further herein. Generally, various embodiments may be disclosed relative to a human subject. It is understood, however, that various disclosed systems, such as navigation or tracking systems, may be used relative to any subject or system that may have an outer hull or shell that may encompass internal components or operations. For example, an air frame or automobile frame may obscure internal components, which may be selected to be operated on in a selected procedure. The selected procedure may include removal, replacement, or the like of various components of any non-animate or inanimate system. Accordingly, it is understood that a discussion herein relative to a subject, such as a human subject, is merely exemplary.

Further, as discussed herein, a navigation system may include tracking various components, such as an instrument, relative to a reference frame within a coordinate system or space. In various embodiments, the coordinate space may include a subject coordinate space or a real space defined by real space relative to the subject. Additional coordinate spaces may include image space that has an image coordinate space defined an image of the subject. A pose of an instrument, as discussed above that may include a position and orientation of the instrument, may be illustrated relative to, for example superimposed on, the image with a graphical representation for viewing by a user. Such illustrations may require or use registration between a subject space or subject coordinate space and an image coordinate space or image space.

A method to register a subject space defined by a subject to an image space may include those disclosed in U.S. Pat. Nos. 8,737,708; 9,737,235; 8,503,745; and 8,175,681; all incorporated herein by reference.

FIG. 1, according to various embodiments, is a diagrammatic view illustrating an overview of a procedure room or arena. In various embodiments, the procedure room may include a surgical suite. The surgical suite may include a navigation system 26 that can be used for various procedures, such as those relative to a subject 30.

The navigation system 26 can be used to track the pose of one or more tracking devices, and the tracking devices may include a subject tracking device or dynamic reference frame (DRF) 58, an imaging system tracking device 62, and/or a tool tracking device 66. It is understood that other tracking devices may also be included, such as a user or clinician tracking device alone or in combination with other systems (e.g. augmented reality systems). A tool 68 may be any appropriate tool such as a drill, forceps, or other tool operated by a user 72. The tool 68 may also include an implant, such as a spinal implant or orthopedic implant. It should further be noted that the navigation system 26 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 26 and the various instruments may be used in any appropriate procedure, such as one that is generally minimally invasive or an open procedure.

An imaging device 80 may be used to acquire pre-, intra-, or post-operative or real-time image data of a subject, such as the subject 30. It will be understood, however, that any appropriate subject can be imaged and any appropriate procedure may be performed relative to the subject. In the example shown, the imaging device 80 comprises an O-Arm® imaging device sold by Medtronic Navigation, Inc. having a place of business in Louisville, Colorado, USA. The imaging device 80 may have a generally annular gantry housing 82 in which an image capturing portion is moveably placed. The image capturing portion may include an x-ray source or emission portion and an x-ray receiving or image receiving portion located generally or as practically possible 180 degrees from each other and mounted on a rotor relative to a track or rail. The image capturing portion can be operable to rotate 360 degrees during image acquisition. The image capturing portion may rotate around a central point or axis, allowing image data of the subject 30 to be acquired from multiple directions or in multiple planes. The imaging device 80 can include those disclosed in U.S. Pat. Nos. 7,188,998; 7,108,421; 7,106,825; 7,001,045; and 6,940,941; all of which are incorporated herein by reference, or any appropriate portions thereof. In one example, the imaging device 80 can utilize flat plate technology having a 1,720 by 1,024 pixel viewing area.

The position of the imaging device 80, and/or portions therein such as the image capturing portion, can be precisely known relative to any other portion of the imaging device 80. The imaging device 80, according to various embodiments, can know and recall precise coordinates relative to a fixed or selected coordinate system. This can allow the imaging system 80 to know its position relative to the patient 30 or other references. In addition, as discussed herein, the precise knowledge of the position of the image capturing portion can be used in conjunction with a tracking system to determine the position of the image capturing portion and the image data relative to the tracked subject, such as the patient 30.

The imaging device 80 can also be tracked with the image tracking device 62. The image data defining an image space acquired of the patient 30 can, according to various embodiments, be inherently or automatically registered relative to an object space. The object space can be the space defined by a patient 30 in the navigation system 26. The automatic registration can be achieved by including the tracking device 62 on the imaging device 80 and/or the determinable precise pose of the image capturing portion. According to various embodiments, as discussed herein, imageable portions, virtual fiducial points and other features can also be used to allow for registration, automatic or otherwise. It will be understood, however, that image data can be acquired of any subject which will define subject space. Patient space is an exemplary subject space. Registration allows for a map between patient space and image space.

The patient 30 can also be tracked as the patient moves with the patient tracking device, DRF, or tracker 58. Alternatively, or in addition thereto, the patient 30 may be fixed within navigation space defined by the navigation system 26 to allow for registration. As discussed further herein, registration of the image space to the patient space or subject space allows for navigation of the instrument 68 with the image data. When navigating the instrument 68, a pose of the instrument 68 can be illustrated relative to image data acquired of the patient 30 on a display device 84. Various tracking systems, including at least one of an optical localizer 88 or an electromagnetic (EM) localizer 94, can be used to track the instrument 68. As discussed herein, in various embodiments, the localizer 94 may transmit a signal that is received by the tracking device 66, or other appropriate tracking device. In addition, an appropriate antenna, e.g. a coil, may also be provided as a received. For example, a calibration receiver 95 (e.g. a coil) may be provided to receive a signal form the localizer 94. The calibration receiver 95 may be included in any appropriate portion of the navigation system 26, such as a controller 110, as discussed further herein. It is understood by one skilled in the art that the calibration receiver 95 need not be incorporated into the navigation system 26 during a use, but may be provided or used during an initial (e.g. factory) production or calibration of the navigation system 26. In various embodiments, the calibration receiver 95 may receive the signal from the localizer 94 in a manner similar to the tracking device 66 and be used for various purposes, as discussed herein.

More than one tracking system can be used to track the instrument 68 in the navigation system 26. According to various embodiments, tracking systems can include an electromagnetic tracking (EM) system having the EM localizer 94 and/or an optical tracking system having the optical localizer 88. Either or both of the tracking systems can be used to tracked selected tracking devices, as discussed herein. It will be understood, unless discussed otherwise, that a tracking device can be a portion trackable with a selected tracking system. A tracking device need not refer to the entire member or structure to which the tracking device is affixed or associated.

It is further appreciated that the imaging device 80 may be an imaging device other than the O-Arm® imaging device and may include in addition or alternatively a fluoroscopic C-arm. Other exemplary imaging devices may include fluoroscopes such as bi-plane fluoroscopic systems, ceiling mounted fluoroscopic systems, cath-lab fluoroscopic systems, fixed C-arm fluoroscopic systems, isocentric C-arm fluoroscopic systems, 3D fluoroscopic systems, etc. Other appropriate imaging devices can also include MRI, CT, ultrasound, etc.

In various embodiments, an imaging device controller 96 may control the imaging device 80 and can receive the image data generated at the image capturing portion and store the images for later use. The controller 96 can also control the rotation of the image capturing portion of the imaging device 80. It will be understood that the controller 96 need not be integral with the gantry housing 82, but may be separate therefrom. For example, the controller may be a portion of the navigation system 26 that may include a processing and/or control system 98 including a processing unit or processing portion 102. The controller 96, however, may be integral with the gantry 82 and may include a second and separate processor, such as that in a portable computer.

The patient 30 can be positioned, including fixed, on an operating table 104. According to one example, the table 104 can be an Axis Jackson® operating table sold by OSI, a subsidiary of Mizuho Ikakogyo Co., Ltd., having a place of business in Tokyo, Japan or Mizuho Orthopedic Systems, Inc. having a place of business in California, USA. Patient positioning devices can be used with the table, and include a Mayfield® clamp or those set forth in U.S. Pat. App. Pub. No. 2004/0199072, published Oct. 7, 2004 (U.S. patent application Ser. No. 10/405,068) entitled "An Integrated Electromagnetic Navigation And Patient Positioning Device", which is hereby incorporated by reference.

The position of the patient 30 relative to the imaging device 80 can be determined by the navigation system 26. The tracking device 62 can be used to track and determine a pose of at least a portion of the imaging device 80, for example the gantry or housing 82. The patient 30 can be tracked with the dynamic reference frame 58, as discussed further herein. Accordingly, the position of the patient 30 relative to the imaging device 80 can be determined. Further, the pose of the imaging portion can be determined relative to the housing 82 due to its precise position on the rail within the housing 82, substantially inflexible rotor, etc. The imaging device 80 can include an accuracy of within 10 microns, for example, if the imaging device 80 is an O-Arm® imaging device sold by Medtronic Navigation, Inc. having a place of business in Louisville, Colorado Precise positioning of the imaging portion is further described in U.S. Pat. Nos. 7,188,998; 7,108,421; 7,106,825; 7,001,045; and 6,940,941; all of which are incorporated herein by reference, According to various embodiments, the imaging device 80 can generate and/or emit x-rays from the x-ray source that propagate through the patient 30 and are received by the x-ray imaging receiving portion. The image capturing portion generates image data representing the intensities of the received x-rays. Typically, the image capturing portion can include an image intensifier that first converts the x-rays to visible light and a camera (e.g. a charge-coupled device) that converts the visible light into digital image data. The image capturing portion may also be a digital device that converts x-rays directly to digital image data for forming images, thus potentially avoiding distortion introduced by first converting to visible light.

Two dimensional and/or three dimensional fluoroscopic image data that may be taken by the imaging device 80 can be captured and stored in the imaging device controller 96. Multiple image data taken by the imaging device 80 may also be captured and assembled to provide a larger view or image of a whole region of a patient 30, as opposed to being directed to only a portion of a region of the patient 30. For example, multiple image data of the patient's 30 spine may be appended together to provide a full view or complete set of image data of the spine.

The image data can then be forwarded from the image device controller 96 to the navigation computer and/or processor system 102 that can be a part of a controller or work station 98 having the display 84 and a user interface 106. It will also be understood that the image data is not necessarily first retained in the controller 96, but may also be directly transmitted to the work station 98. The work station 98 can provide facilities for displaying the image data as an image 108 on the display 84, saving, digitally manipulating, or printing a hard copy image of the received image data. The user interface 106, which may be a keyboard, mouse, touch pen, touch screen or other suitable device, allows the user 72 to provide inputs to control the imaging device 80, via the image device controller 96, or adjust the display settings of the display 84. The work station 98 may also direct the image device controller 96 to adjust the image capturing portion of the imaging device 80 to obtain various two-dimensional images along different planes in order to generate representative two-dimensional and three-dimensional image data.

With continuing reference to FIG. 1, the navigation system 26 can further include the tracking system including either or both of the electromagnetic (EM) localizer 94 and/or the optical localizer 88. The tracking systems may include the controller and interface portion 110. The controller 110 can be connected to the processor portion 102, which can include a processor included within a computer. The EM tracking system may include the STEALTHSTATION® AXIEM™ Navigation System, sold by Medtronic Navigation, Inc. having a place of business in Louisville, Colorado; or can be the EM tracking system described in U.S. patent application Ser. No. 10/941,782, filed Sep. 15, 2004, and entitled "METHOD AND APPARATUS FOR SURGICAL NAVIGATION"; U.S. Pat. No. 5,913,820, entitled "Position Location System," issued Jun. 22, 1999; and U.S. Pat. No. 5,592,939, entitled "Method and System for Navigating a Catheter Probe," issued Jan. 14, 1997; all of which are herein incorporated by reference. It will be understood that the navigation system 26 may also be or include any appropriate tracking system, including a STEALTHSTATION® TREON® or S7™ tracking systems having an optical localizer, that may be used as the optical localizer 88, and sold by Medtronic Navigation, Inc. of Louisville, Colorado Other tracking systems include an acoustic, radiation, radar, etc. The tracking systems can be used according to generally known or described techniques in the above incorporated references. Details will not be included herein except when to clarify selected operation of the subject disclosure.

Wired or physical connections can interconnect the tracking systems, imaging device 80, etc. Alternatively, various portions, such as the instrument 68 may employ a wireless communications channel, such as that disclosed in U.S. Pat. No. 6,474,341, entitled "Surgical Communication Power System," issued Nov. 5, 2002, herein incorporated by reference, as opposed to being coupled directly to the controller 110. Also, the tracking devices 62, 66, can generate a field and/or signal that is sensed by the localizer(s) 88, 94. In various embodiments, the instrument tracking device 66, and/or other appropriate tracking devices, may communicate with a wireless signal 113, as discussed herein, with the controller 110 and/or the array 94. In various embodiments, the array 94 may operate with a spread spectrum signal to communicate with the tracking device 66.

Various portions of the navigation system 26, such as the instrument 68, and others as will be described in detail below, can be equipped with at least one, and generally multiple, of the tracking devices 66. The instrument can also include more than one type or modality of tracking device 66, such as an EM tracking device and/or an optical tracking device. The instrument 68 can include a graspable or manipulable portion at a proximal end and the tracking devices may be fixed near the manipulable portion of the instrument 68. It is understood, however, that the tracking device may also be placed at a distal or intervention end of the instrument 68.

Additional representative or alternative localization and tracking system is set forth in U.S. Pat. No. 5,983,126, entitled "Catheter Location System and Method," issued Nov. 9, 1999, which is hereby incorporated by reference. The navigation system 26 may be a hybrid system that includes components from various tracking systems.

According to various embodiments, the navigation system 26 can be used to track the instrument 68 relative to the patient 30. The instrument 68 can be tracked with the tracking system, as discussed herein, such as by tracking and determining a pose of the tracking device 66. Image data of the patient 30, or an appropriate subject, can be used to assist the user 72 in guiding the instrument 68. The image data, however, is registered to the patient 30. The image data defines an image space that is registered to the patient space defined by the patient 30. The registration can be performed as discussed herein, automatically, manually, or combinations thereof.

Generally, registration allows a map, also referred to as a registration map, to be generated of the physical pose of the instrument 68 relative to the image space of the image data. The map allows the tracked pose of the instrument 68 to be displayed on the display device 84 relative to the image data 108. It is understood that the display device 84 may be any appropriate display device, or include more than a single display device, such as including augmented reality viewers, head mounted displays, etc. A graphical representation 68i, also referred to as an icon, can be used to illustrate the pose (e.g. three-dimensional coordinate location and one or more degree of freedom orientation) of the instrument 68 relative to the image 108.

With continuing reference to FIG. 1 and additional reference to FIG. 2, a subject registration system or method can use the subject tracking device 58. The tracking device 58 may include portions or members 120 that may be trackable, but may also act as or be operable as a fiducial assembly. The fiducial assembly 120 can include a clamp or other fixation portion 124 and the imageable fiducial body 120. It is understood, however, that the members 120 may be separate from the tracking device 58. The fixation portion 124 can be provided to fix any appropriate portion, such as a portion of the anatomy. As illustrated in FIG. 1, the fiducial assembly 120 can be interconnected with a portion of a spine such as a spinous process of the subject 30.

The fixation portion 124 can be interconnected with the spinous process in any appropriate manner. For example, a pin or a screw can be driven into the spinous process. Alternatively, or in addition thereto, a clamp portion 124 can be provided to interconnect the spinous process. The fiducial portions 120 may be imaged with the imaging device 80. It is understood, however, that various portions of the subject (such as a spinous process) may also be used as a fiducial portion.

In various embodiments, when the fiducial portions 120 are imaged with the imaging device 80, image data is generated that includes or identifies the fiducial portions 120. The fiducial portions 120 can be identified in image data automatically (e.g. with a processor executing a program), manually (e.g. by selection an identification by the user 72), or combinations thereof (e.g. by selection an identification by the user 72 of a seed point and segmentation by a processor executing a program). Methods of automatic imageable portion identification include those disclosed in U.S. Pat. No. 8,150,494 issued on Apr. 3, 2012, incorporated herein by reference. Manual identification can include selecting an element (e.g. pixel) or region in the image data wherein the imageable portion has been imaged. Regardless, the fiducial portions 120 identified in the image data can be used as fiducial points or positions that can be used to register the image data or the image space of the image data with patient space.

In various embodiments, to register an image space or coordinate system to another space or coordinate system, such as a navigation space, the fiducial portions 120 that are identified in the image 108 may then be identified in the subject space defined by the subject 30, in an appropriate manner. For example, the user 72 may move the instrument 68 relative to the subject 30 to touch the fiducial portions 120, if the fiducial portions are attached to the subject 30 in the same position during the acquisition of the image data to generate the image 108. It is understood that the fiducial portions 120, as discussed above in various embodiments, may be attached to the subject 30 and/or may include anatomical portions of the subject 30. Additionally, a tracking device may be incorporated into the fiducial portions 120 and they may be maintained with the subject 30 after the image is acquired. In this case, the registration or the identification of the fiducial portions 120 in a subject space may be made. Nevertheless, according to various embodiments, the user 72 may move the instrument 68 to touch the fiducial portions 120.

The tracking system, according to various embodiments, may track the pose of the instrument 68 due to the tracking device 66 attached thereto. This allows the user 72 to identify in the navigation space (which may include or be a portion of the subject space) the poses (including, for example, six degree of freedom information including locating and orientation) of the fiducial portions 120 that are identified in the image 108. After identifying the positions of the fiducial portions 120 in the navigation space, the map may be made between the subject space defined by the subject 30 in a navigation space and the image space defined by the image 108. Accordingly, identical or known locations allow for registration as discussed further herein.

During registration, the map is determined between the image data coordinate system of the image data such as the image 108 and the patient space defined by the patient 30. Once the registration occurs, the instrument 68 can be tracked with the tracking system that is registered to the image data to allow an identification and illustration of a pose of the tracked instrument 68 as an icon superimposed on the image data. Registration of the image 108 (or any selected image data) to the subject 30 may occur at any appropriate time.

In various embodiments, the image space 108 and the subject space defined by the subject 30 may be registered according to a method 150. As discussed above, the image to patient registration may include acquiring and/or accessing (e.g. from a memory system having the image data stored thereon) image data of a subject, such as the subject 30, with fiducials in block 152. The image data of the subject 30 may be any appropriate image data, such as image data acquired with the imaging system 80. Further, the fiducials may include the fiducial portions 120, as discussed above, and/or appropriate anatomical portions of the subject 30. For example the fiducial portions may include portions of the anatomy such as the spinous process of the subject 30. Nevertheless, the acquired image data may include the fiducials therein. Once the image data is acquired of the subject with the fiducials, identification of the fiducials in the image space may occur in block 154.

The identification of the fiducials in the image space in block 154 may occur, as also discussed above. For example, an automatic identification of the fiducials may be made in the image data that defines the image space, such as through automatic segmentation of the fiducial portions within the image. Also manual identification and/or combination manual-and-automatic identification may be used to determine the fiducials in the image space. The combination may include the user 72 identifying one or more pixels as seed pixels and a processor executing a segmentation program based on the seed pixels.

The identification of the fiducials in a subject space and/or navigation space occurs in block 156. The subject space may be coextensive with the navigation space and/or may overlap. Generally, the navigation space is the volume that may be tracked with the tracking system, such as the localizer 94 and may encompass all or a portion of the subject or patient 30. The identification of the fiducials in the navigation space may occur in various manners such as moving a trackable instrument, such as the instrument 68, relative to the fiducial portions 120 (which may also be a tracking device) and/or the spinous process. The tracking system of the navigation system 26 may track the instrument 68 and the navigation system 26 may include an input to input the portions that are the fiducial portions 120 in the navigation space. The determination or identification of the pose (e.g. including at selected degree of freedom information including three dimensional location and orientation) of the fiducials in the navigation space may then be used to form the map, between two or more coordinate systems, in block 160.

Determination of the map determined in block 160 may be a correlation or registration of the coordinate system of the image space to the coordinate system of the navigation space relative to and/or including the subject 30. The map allows for a determined pose of a tracked portion in the navigation space to be mapped to an equivalent or identical pose in the image. Once the mapped pose is determined, the pose may be illustrated or displayed with the display relative to the image 108, such as by the superimposing of the icon 68i on or relative to the image 108.

The image to patient registration allows for the illustration of tracked instruments or items relative to the image 108. Without the registration, however, any element not trackable or registered to the image 108 may not be appropriately or precisely illustrated at a real world pose relative to the image 108. Thus, registration may allow for illustration, such as with the icon 68i, of a determined pose of the instrument 68 relative to the subject 30.

After the registration of the image space to the patient space, the instrument 68 can be tracked relative to the image 108. As illustrated in FIG. 1, the icon 68i representing a pose (which may include a 6 degree of freedom pose (including 3 dimensional location and 3 degree of freedom orientation)) of the instrument 68 can be displayed relative to the image 108 on the display 84. Due to the registration of the image space to the patient space, the pose of the icon 68i relative to the image 108 can substantially identify or mimic the pose of the instrument 68 relative to the patient 30 in the patient space. As discussed above, this can allow a navigated procedure to occur.

With additional reference to FIGS. 2 and 3, and continuing reference to FIG. 1, the localizer 94, which may also be referred to as an array or an antenna array, may be provided in any physical configuration for use of a selected or appropriate procedure. For example, as illustrated in FIG. 1, the localizer 94 is provided or formed to include a selected geometry, such as lobes. In various embodiments the localizer 94, as illustrated in FIG. 3, may be planar or more elongated in shape. The localizer 94 may include a plurality of coils, such as any appropriate number, to generate the navigation field or domain. The navigation field or domain may include a volume 180. The navigation volume 180 is generally sized or moved or placed relative to the subject 30 to allow for navigation of one or more instruments, such as the instrument 68 relative to the subject 30. The instrument 68 may include one or more tracking devices, such as the tool tracking device 66. The array 94 may transmit a signal, as discussed further herein, which may be received by the tracking device 66 or other appropriate tracking devices, such as the subject tracker 58 and/or the imaging device tracker 62.

In various embodiments, the array 94 may be incorporated into the bed or support 104. Alternatively, or in addition thereto, the array 94 may be configured into a shape or size such that the array may be placed below the subject 30 and the subject 30 is placed atop at least a portion of the array 94. In various embodiments, for example, the array 94 may be placed (e.g. fixed) near a lumbar spine of the subject 30 and/or a head of the subject 30 to allow for the navigation field 180 to be centered and/or encompass the selected area of the subject 30 for navigation.

The navigation system 26 may be operated in selected environments, such as in an operating room that includes various other components in addition to the instrument 68. For example, the navigation system 26 may operate in an operating room including the imaging system 80, the operating table 104, and/or other components. Further, a plurality of instruments may be provided for a selected procedure such as the instrument 68 and additional or alternative instruments such as a drill motor 69 that may be placed in a storage or holding area 71. The holding area 71 may include a conductive and/or magnetic material, such as a metal tray or a conductive polymer tray. The tray 71 may be formed of various or selected metal or metal alloys, such as aluminum or stainless steel. In various embodiments, the signal transmitted by the array 94 may be interfered with due to interactions or distortions from various metallic substances, such as the tray 71, the drill 69, the imaging system 80, or other metal portions in the operating room in which the navigation system 26 is placed. Objects or items that may distort the field or signal may be referred to as distorting or distortion objects.

The array 94 may be operated, as discussed further herein, to emit a signal or field. The field emitted by the localizer 94 may be sensed by one or more of the tracking devices, such as the instrument tracking device 66. The field emitted by the array 94, therefore, may be distorted due to the metallic objects in or near the navigation volume 180. Accordingly, the signal received by the tracking device 66, or other tracking devices in the navigation system 26, may include both the emitted signal and distortion. Distortion may be generated by eddy currents in conductive items or magnetizations in magnetic items, which may be referred to herein as "distorting items". The signal received by the tracking device 66 may be transmitted to an appropriate processing system such as one or more processors in the controller 110 and/or the processing unit 102. The signal received may include distortion, if objects are near the navigation volume 180 that cause distortion. Accordingly, a distortion detection and correction (DDC) module 190 (which may include an equalization) may be incorporated or executed by the processing unit 102. The DDC module 190, as discussed further herein, may be used to assist in removing distortion from the signal received by the tracking device 66. Once the distortion is removed in the DDC module 190, a navigation module 198 may also be incorporated into the processing unit 102 and/or executed by the processing unit 102. The navigate module 198 navigates with the corrected signal to determine a pose of the tracking device 66 in the navigation volume 180. Thus, a tracking signal may be emitted by the localizer and received by the tracking device 66. The received tracking signal may include distortion. As discussed above, the navigation of the instrument 68 including in the tracking device 66 may allow for an illustration of a graphical representation 68i of the instrument 68 relative to the image 108 of the subject 30.

Due to the navigation registration, therefore, the user 72 may view a pose of the instrument 68 relative to the subject 30 with the monitor 84. It is understood, by one skilled in the art, that the tracking device 66 may also transmit a signal that is received by the localizer 94. The transmitted signal may be received by the localizer 94 and a similar equalizer and navigation module may be used to determine a pose of the tracking device 66 relative to the subject 30 in a similar manner but where the signal is received by the localizer 94, rather than transmitted by the localizer 94. Further, one skilled in the art will understand that the plurality of instruments may be navigated substantially simultaneously to allow for illustration of a plurality of instruments relative to the image 108 simultaneously when a plurality of instruments are tracked relative to the subject 30 in the navigation volume 180 substantially simultaneously.

The localizer 94, regardless of its configuration or external geometry may include one or more coils 200. The localizer may include an appropriate number of coils 200, such as enough to transmit a signal to resolved at the tracking device 66 to navigate the tracking device 66. The localizer 94, therefore, may include one or more coils 200, including nine or more coils, 12 or more coils 200, or up to 36 coils, or an appropriate number of the coils 200 The coils 200 may be provided in any appropriate number and the number discussed herein is merely exemplary. For example, the localizer 94 may include three coils that are substantially orthogonally oriented and placed relative to one another around a single center or origin. Alternatively, or in addition thereto, one or more coils may be placed and oriented at a selected angle relative to one another within the localizer 94. Regardless of the configuration, the one or more coils generate a navigation field with an electromagnetic (EM) signal that may be sensed by the respective tracking devices, including the tracking device 66, to allow for determination of a pose of the tracking device 66 in space.

With continuing reference to FIG. 1 and additional reference to FIG. 3, the localizer 94 may be configured in any appropriate manner, including those discussed herein. Exemplary illustrated in FIG. 3 is a rectangular localizer assembly. The localizer assembly 94 may include one or more coils 200, such as a first coil 200a. The coil 200a may be included in the localizer 94 along with one or more other coils, such as a second coil 200b. It is understood that any appropriate number of coils may be provided and two coils 200a, 200b is merely exemplary. Further, the localizer 94 may be controlled by the controller 110 and/or have an onboard controller such as a controller or control module 110'. Further, in various embodiments a local power source or converter may be provided at the localizer 94. For example, a power converter or battery may be provided to provide power to the controller 110' and/or the coils 200 to transmit the tracking signal. In various embodiments, an external power source, as an alternative to and/or in addition to the local power source, may transmit power to the controller 110,110' and/or the coils 200 from a location away from the localizer 94.

Regardless of the number or configuration, the respective coils, including the coils 200, may be driven to transmit a signal that may be received by the tracking device 66. In various embodiments, for example, the respective coils 200a, 200b may be placed or incorporated into an "H" bridge configuration or switch system. With reference to the coil 200a, and understanding of the second coil 200b may be incorporated into a similar configuration, the coil 200a may be interconnected between a drive source and a ground with a plurality of switches. In various embodiments, for example, the coil 200a may be integrated into an "H" bridge assembly 220. The "H" bridge assembly 220 may include a plurality of switches including a first switch 222, a second switch 224, a third switch 226 and a fourth switch 228. The switches 222-228 may selectively allow a current to be driven through the coil 200a from a source or voltage source 230 to a ground or outlet 234.

For example, the first switch 222 and the second switch 224 may be closed to allow a voltage to form across the coil 220a and a current to flow through the coil 200a in a first direction. Similarly the third switch 226 and the fourth switch 228 may be closed, with the respective first and second switches 222,224 being open, to allow current to be driven through the coil 200a in a second direction. As discussed above, the controller 110 may be used to control selected switches to pass a current through the coil 200a. The currents pass through the coil 200a to cause signals to be emitted by the coil 200a and to be received by the tracking device 66.

Similarly an "H" bridge 220b may be connected to the coil 200b and operate in a similar manner. The controller 110 and/or control 110' may operate both of the "H" bridge assemblies 220a, 220b to power or transmit a signal through the respective coils 200a, 200b. It is understood that the "H" bridge assemblies may be provided in any appropriate manner such as with manual or physical switches, transistors switches, or any appropriate switches relative to the respective coils. Moreover, as discussed above, any appropriate number of coils may be provided with the localizer 94 to generate navigation field as selected to generate or provide the navigation volume 180. The schematic or illustration of FIG. 3 is merely exemplary for the current discussion.

The coils, such as the coil 200a, may be powered via the "H" bridge assembly 220a to provide a signal for navigation of the instrument 68. The "H" bridge assembly 220a may be provided in the localizer 94 to allow the coil 200a to be driven while maintaining a selected energy or field emission and heat generation of the coil 200a and localizer 94. The localizer 94, therefore, may include an appropriate number of coils such as between 1 and 36 coils, including three coils to 15 coils, while still maintaining a selected field emission and heat generation. The plurality of coils may be driven with the controller 110, 110' in an appropriate manner, as discussed herein, to generate the navigation domain 180.

The tracking system may include the localizer 94, as discussed above. The localizer 94 may be controlled by a controller 110. The localizer 94 may transmit a field or emit a field 113 that may be sensed by the tracking device 66 of the instrument 68. It is understood that other appropriate tracking devices or receiving devices (e.g. the calibration receiver 95) may also sense the field 113 of the localizer 94. The field 113 may be generated in an appropriate manner, such as including or having a spread spectrum. The field 113 may also have, in addition or alternatively, a modulation that may be sensed by the tracking device 66. The field 113 may assist in reducing or eliminating distortion or interference of the filed sensed by the tracking device 66, as discussed further herein, due to an interfering, also referred to as a distorting or distortion, object.

As discussed above the localizer 94 may be controlled by the controller 110, 110' (discussion herein related to the controller 110 is intended to encompass all appropriate controllers, including those discussed above, and reference to only controller 110 is merely for ease of the current discussion), according to an appropriate transmission system. As discussed above, the coil, such as the coil 200a (also discussion herein to the single coil 200a is merely exemplary and for ease of the current discussion), may be powered or connected with the "H" bridge configuration 220a. The "H" bridge configuration 220 may be provided in any appropriate manner including switches (e.g. physical or manual) and/or transistors that may be operated with the controller 110. Regardless, the coil or plurality of coils of the localizer 94 may be operated to transmit with a binary transmission system or scheme including a binary near orthogonal (BNO) transmission system or scheme. The coil or plurality of coils of the localizer 94 may be operated to transmit signals as sets of binary near orthogonal (BNO) sequences for efficient recovery of both the transmitted signals and the impulse responses of the system and the impulse responses of distorters (also referred to as distortion items) in the navigation field.

Under the BNO scheme, a pseudorandom binary (PRB) sequence, also referred to as a pseudo-noise (PN) sequence with one such type being a maximum length (ML) sequence, may be generated with the controller 110 to be transmitted by the localizer 94 as the tracking signal 113. The tracking signal 113 transmission may be also be a spread spectrum transmission such that it is spread across a large or broad frequency spectrum or over a large or broad frequency spectrum which may also be segmented due to time.

The PN sequence may be provided in a generally orthogonal or near orthogonal manner to provide an appropriate transmission for receiving by the tracking device 66, or other appropriate tracking device. The tracking signal 113 may be used for navigation of the tracking device 66. Further, discussion of the single tracking device 66, or any appropriate or single portion of the navigation system 26 herein, is merely exemplary and intended for the ease of the current discussion unless specifically indicated otherwise.

In various embodiments, therefore, cyclic shifts or offsets of the same repeating PN sequence are transmitted, one on each transmit coil. Statistically, an autocorrelation function of the PN sequence is equal to 1 at an offset zero and $$-\frac{1}{2^n - 1}$$

at all other offsets, where the sequence length equals $2^n - 1$ and the number of sequence generator bits equals n with n=14 useable in various embodiments. Cyclic shifts or offsets of the PN sequence may be understood to be nearly orthogonal to one another in the sense that any pair of distinct shifts of the sequence are poorly correlated for any sufficiently-large value "n". Systems which demodulate all cyclic shift amplitudes in the repeating PN frame may recover the associated coil signal amplitudes by multiplying by the inverse of the PN leakage matrix, which has 1 on the diagonals and $$-\frac{1}{2^n - 1}$$

elsewhere. In addition, when the PN offsets of the transmit coils have spacings greater than distorter response durations (i.e. a time of receiving a distortion from a distorting object), this method may recover the distorter impulse response to each generator coil. In various embodiments, an offset may be 10 sequence generator bits. Select methods may be used to perform the calculations, discussed above, including the Walsh-Hadamard transform via the fast-Walsh-transform based method as described "Impulse response measurements using MLS", by Jens Hee, http://www.jenshee.dk/signalprocessing/mls.pdf (2003). The method may be used to directly perform both the demodulation (multiplication by the PN sequence at all offsets) and the leakage inversion.

As discussed above, the controller 110 may power the coil 200a to transmit a signal that may be received by the tracking device 66. It is understood, as discussed above, that the tracking device 66 may also transmit a signal in a similar manner, as discussed herein, that is received by the one or more coils of the localizer 94. The tracking device 66 may also include a plurality of coils, such as coils that are oriented substantially orthogonally to one another around a central point and/or separated from one another. In various examples, the tracking device 66 may include a plurality of coils, such as three coils 66a, 66b, and 66c. The tracking device 66, or any appropriate receiving coil device (e.g. the calibration receiver 95), however, may include a selected number of coils For example, one coil, more than one coil, at least three coils, or more than three coils, such as six coils. The number of receiving coils may be appropriate to navigate the tracking device 66. Each of the coils may be formed of a selected conductive material to have a current induced therein by the signal from the localizer. In various embodiments the coils may include wire wrapped around a center and/or traces formed on a printed circuit board (PCB). Nevertheless, the tracking device 66, as discussed herein, may receive a signal from the localizer 94 although it is understood by one skilled in the art that the localizer may receive a signal from the tracking device and vice versa.

In various embodiments, as discussed above, the controller 100 may cause or signal the one or more coils, such as the coil 200a, of the localizer 94 to transmit a signal which may also be referred to as a tracking signal, as discussed herein. The coils 200 may be formed of a selected conductive material, such as a coil of metal or metal alloy wire. An impulse response(s) is(are) calculated from the received, continuously-transmitted BNO signal set from the transmit coils. The tracking signals are a set of BNO signals that include the same binary PN signal that is delayed by a different amount for each coil of the localizer. An inter-coil offset may include a selected time delay spacing is greater than the length of the metallic distorter impulse response length. The signal delay or spacing may include a selected duration, such as about 1 to 20 milliseconds, including 5 to 10 milliseconds, with an equivalent or greater spacing between signals from each coil.

The tracking signal transmitted may be in any appropriate frequency range such as in a frequency range of about 5 hertz (Hz) to about 30 megahertz (MHz), further including about 10 Hz to about 3 MHz, and further including about 10 Hz to about 400 kilohertz (kHz). The signal may be transmitted at a selected frequency or over a range of frequencies in a spread spectrum fashion in the selected range. For example, a spread spectrum signal may transmit a signal across a spectrum of about 1 Hz to 30 MHz, including about 10 Hz to about 400 kHz that is transmitted at a sample rate at or about 375 kHz. In various embodiments, the control over the signal is the sample rate and waveform, which may include a binary drive waveform. The spectrum may be flat from the direct current (D.C.) to the sample rate. In various embodiments, therefore, the spectrum is flat when navigating the instrument, as discussed above. The controller via the H-bridge configuration may drive the coils, such as the coil 200a, at the selected frequency or across a spread spectrum of frequency near the selected frequency.

As discussed above, the localizer 94 may transmit a signal from the controller 110 through one or more of the coils, such as the coil 200a. As further discussed above the H-bridge configuration 220a may be provide in any appropriate configuration such as including transistors at the switches 222-228. Accordingly, the controller 100 may cause the coil 200a to transmit a signal (e.g. an electromagnetic signal) to be received by the tracking device 66. The navigation system 26, however, may transmit a magnetic signal using any appropriate manner, including but not limited to, H-bridge circuits and closed loop analog circuits.

Figure 4B:
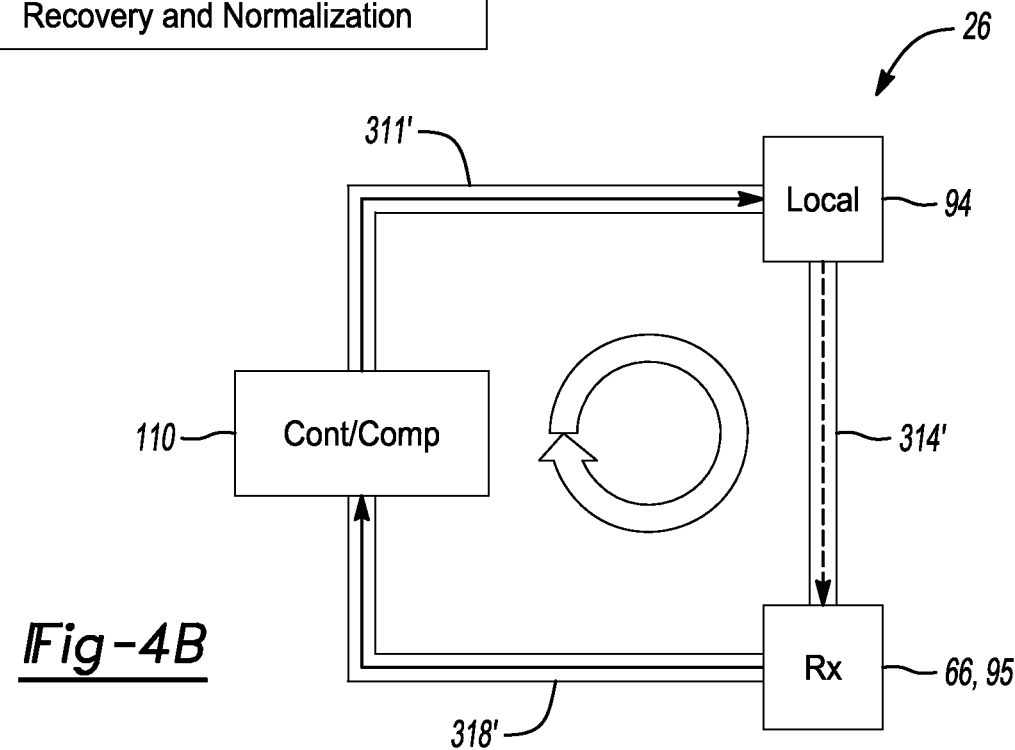
FIG. 4B is a schematic illustration of a navigation system calibration and equalization method of FIG. 4A.

With reference to FIG. 4A and FIG. 4B, a transmit to receive calibration and/or equalization (C/E) procedure 300 and related schematic thereof is illustrated. As discussed herein, with reference to FIGS. 5A and 5B and FIGS. 6A and 6B, various additional and/or alternative C/E methods and systems may be used. In various embodiments, the C/E may include or be performed as a full system C/E and/or as various sub-channels or components.

With initiate reference to FIGS. 4A and 4B, the C/E procedure 300 may be a full system C/E also referred to as an end-to-end C/E include various procedural steps such as starting in start block 310. After starting in the start block 310, a calibration or equalization signal may be generated from the controller 110 and sent to the localizer 94 (which may also be referred to as a transmitter) in block 311, illustrated schematically as 311'. The calibration signal may then be transmitted from the localizer 94 in block 314, illustrated schematically as 314', to be received, such as at the calibration receiving coil 95 and/or other appropriate receiver, such as the tracking device 66. Transmission of the calibration signal in block 314 may include transmitting a calibration signal according to the spread spectrum scheme, as discussed above. Further, the transmission may include the PN signal from the coil 200a and the other coils 200 of the localizer 94.

As discussed above the signal sent by the coils may be generated as a PN sequence. The PN sequence may include selected lengths, such as a length of 1023 to 16383 in a sequence. The various coils may be off-set relative to one another by an appropriate number such as about 1023 length to achieve a distinction between the several coils 200 of the localizer 94. The PN sequence may be generated and transmitted with the controller 110. The transmitted signal at the selected frequency or spread spectrum, as discussed above, is to be respectively received by the tracking device 66 and/or other appropriate receiver, such as the calibration receiver 95 (even with reference to only one receiver coil herein). The coils 200, therefore, may generate or transmit the signal in an appropriate time, such as in sequence or substantially simultaneously to be received by the tracking device 66. The PN sequence may be generated according to any appropriate technique. In various embodiments, for example, a PN sequence may be generated with an irreducible polynomial.

The tracking device 66 may receive the transmitted calibration signal and transmit the received signal to the controller 110 in block 318, illustrated schematically as 318'. The received calibration signal in block 318 may then be sampled and various calculations may be performed by the controller 120 (or any appropriate processor system) to perform a calibration in block 322. The calibration in block 322 may include calibration based upon various parameters such as transmission distance, field strength at a known pose, or other appropriate calibration parameters.

Calibration in block 322 can be performed according to appropriate techniques, as discussed below. In various embodiments, calibration in block 322 could include impulse response normalization via placing the tracking device 66 (e.g. including coils) at a fixed pose with respect to the localizer 94 including one or more of the coils 200. Transmission calibration could include transmitted magnetic field measurements via an external or separate magnetometer and/or as previously characterized at the tracking device 66 (e.g. sensing coil). Receiver coil calibration could include received voltage measurement via external multimeter at or near the tracking device and/or as previously characterized with the tracking device 66 (e.g. sensing coil).

The calibration in block 322 may include ensuring a known or clean room field strengths at selected poses. The calibration may include placing the localizer 94 at a selected location, which may also be referred to as an origin, and moving the tracking device 66 or an appropriate receiving tracking device at a plurality of known poses (i.e. locations and orientations) relative to the origin. The signal received by the tracking device 66 may then be used in the calibration 322. For example, the calibration may include or account for possible distortion or noise in the signal as the signal starts and travels through transmitter (e.g. localizer 94) circuitry and filters, transmitter coils, air, tracking device 66 coils, circuitry and filters related to or included with the tracking device 66, and then as the signal is received back at the controller.

The calibration, regardless how determined including as discussed above, may then be equalized in an equalization step in block 324. In the equalization in block 324 an equalization is determined between each of the coils 200 of the localizer 94 and the tracking device 66. Each transmit coil 200 and the tracking device 66 may be equalized for impulse response recovery and normalization of the signal. It is understood that discussion of the tracking device 66 may include discussion of a plurality of coils in the tracking device 66, such as three coils, as discussed above. Accordingly, equalization may be between each of the coils 200 of the localizer 94 and each of the coils of the tracking device 66. For example, between the coil 200a and each of the coils 66a, 66b, and 66c.

Equalization includes removing distortion and/or accounting for noise of the system, including from the controller 110 and the various circuits of the localizer 94 and receiver 66 to allow recovery of a discreet time binary signal from an interference free system. Generally, the equalization is performed by removing distortions of the drive and reception hardware and is to leave only the signal and noise from any external distortion responses. In particular, a binary unitary magnitude pseudo-noise signal measured as a voltage at the receive coil of the tracking device 66 may be measured and an inverse thereof is computed. The equalization then convolves the determined inverse with the signal received at the tracking device 66 (i.e. coils in the tracking device 66) to remove the effects of the localizer 94 and the tracking device 66 and the hardware associated therewith to leave the drive signal from the controller 110 and noise or external distortions in the field.

The equalization is performed by determining coefficients. In particular, an algorithm may be used to determine the coefficients in a test or calibration equalization determination. Equalization may be performed in any appropriate manner, including those generally understood by one skilled in the art. For example, optimize and combine finite impulse response (FIR) and bidirectional infinite impulse response (IIR) filters may be used to equalize channels. The determined coefficients may be used to remove hardware distortion in the equalization between the localizer coil 200 and any coil of the tracking device 66.

Therefore, equalization block 324 may be used to generate or determine a signal that is without distortion due to the hardware of the localizer 94 transmitting via the coils 200 and being received at the tracking device 66 and the coils included therein. Thus, the equalized signal may be used to determine a pose of the tracking device in a field generated by the localizer 94. As discussed above, the localizer 94 may transmit a signal according to BNO scheme where each coil 200 is offset from another coil by about 1023 bits in the PN sequence.

In various embodiments, as briefly noted above, a selected sub-channel or sub-portion of the navigation system 26 may be calibrated and equalized. For example, with reference to FIGS. 5A and 5B, the respective sub-channels of/to each the transmitter or localizer 94 and/or the receiver or tracking device 66 may be individually calibrated and equalized. This may be in addition to and/or alternatively to calibrating and equalizing the entire system, and end, as discussed above and illustrated in FIGS. 4A and 4B.

Figure 5A:
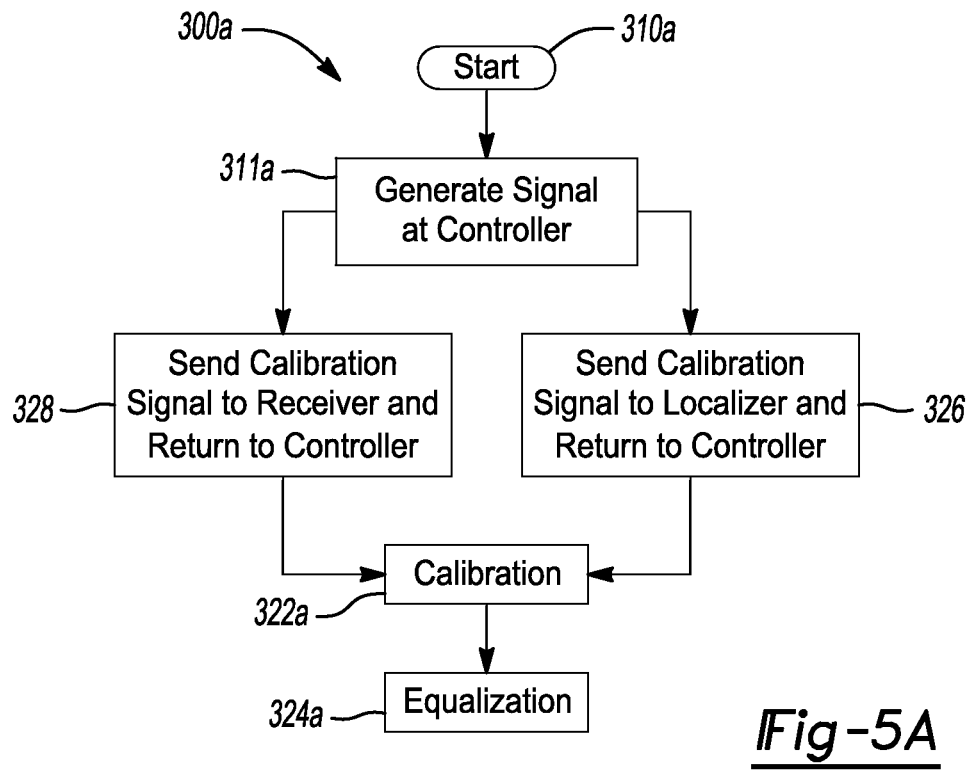
FIG. 5A is a flowchart of a equalization in a spread spectrum navigation system, according to various embodiments.
Figure 5B:
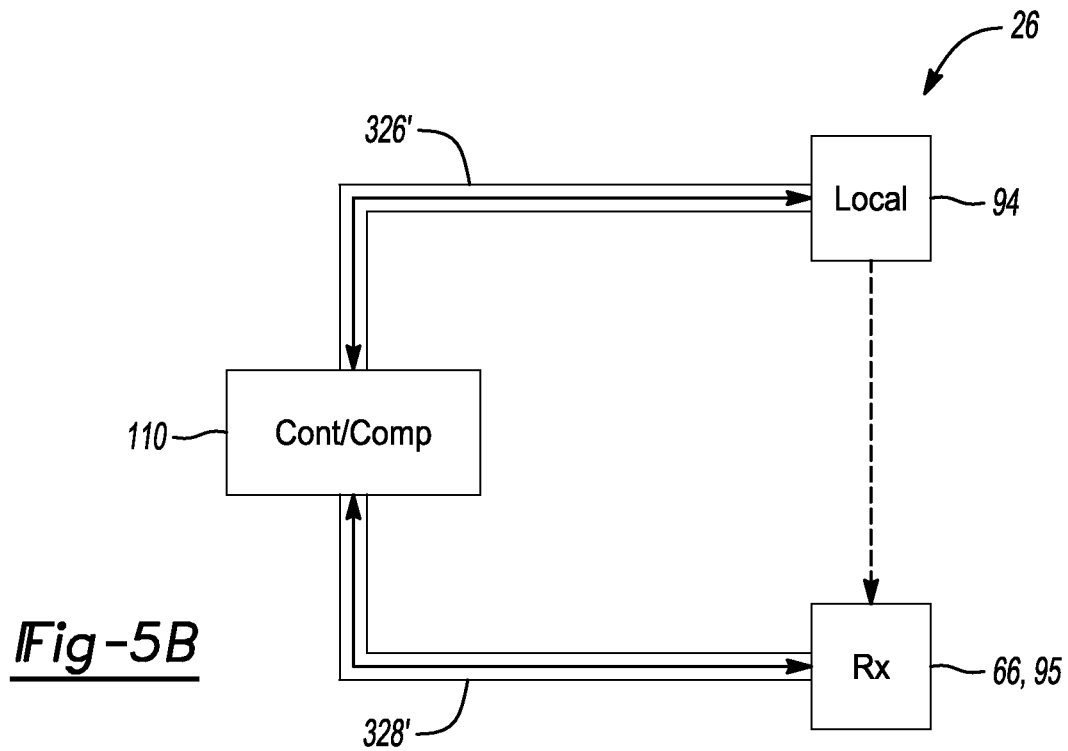
FIG. 5B is a schematic illustration of a navigation system calibration and equalization method of FIG. 5A.

With initial reference to FIG. 5A, a method 300a for calibration and equalization is illustrated. The method 300a may include portions similar to those discussed above in the method 300, and like reference numerals will be used augmented with a lowercase "a". Accordingly, the method 300a may begin at block 310a. The process 300a may then move to block 311a to generate a signal with the controller, such as the controller 110. The signal that is generated may include the PN sequence, as discussed above. Therefore, generating the signal at the controller in block 311a is similar to the generation of the signal in block 311 as discussed above. The generation of the signal and the controller 311a may then be sent through and/or to various components of the navigation system 26, including those as discussed above.

The calibration signal may be sent to the localizer in block 326, illustrated schematically as line 326'. The signal may be sent to the various components from the controller 110 to the localizer 94, including various circuitry and filters, the transmitter coils (e.g. coils 200), and other components between the controller 110 and the localizer 94 and/or including the localizer 94. The signal sent to the localizer 94 may then be transmitted back to the controller 110, after having passed through all of the components of the localizer portion of the navigation system 26. Therefore, the controller 110 may receive a signal returned from the localizer components, such as transmitted from the coils and/or return through a return line to the controller 110, after having passed through all of the components of the localizer 94 portion.

The controller 110 may also transmit a signal to the receiving coils, such as the tracking device 66 and/or the calibration receiver 95 (also referred to herein as the receiver). The signal transmitted to the receiver 66 may be substantially identical to the signal transmitted to the localizer 94. Moreover, the signals may be transmitted substantially simultaneously and/or sequentially. Thus, the signal generated from the controller 110 may also be transmitted to the receiver 66 such as through all of the components thereof, including the receiver circuitry and/or filters, the sensor receive coils (e.g. of the tracking device 66) including all of the selected or appropriate components thereof. The signal may then be returned to the controller 110 after having passed through all of the components such as the controller 110 receives the return signal from the receiver 66.

Accordingly, both of the blocks 326 and 328 may include two components including a transmission and return signal from the respective components including the localizer and the receiver. In other words, the signal may be sent from the controller 110 and return to the controller 110 for calibration and equalization. Accordingly, rather than only or requiring a signal to be transmitted to the localizer 94 which is then transmitted and received by the receiver 66, and then transmitted back to the controller 110, the signal may be sent and returned from each of the separate components as a separate sub-channel calibration and equalization.

The return signals may then be further processed by the controller 110 or appropriate processor system, as discussed above. Calibration may occur in block 322a in a manner similar to that discussed above. The calibration may include various calibration techniques or measurements, similar to those discussed above. For example, the calibration can include measurements of fields such as with a selected magnetometer and/or as previously characterized by the respective coils in the localizer 94 and/or the receiver 66. The calibration signal and/or information may then be used for equalization in block 324a. Again the equalization in block 324a may include that as discussed above for equalization of the signal in the navigation system 26.

Accordingly, calibration and equalization of the navigation system 26 may include separate or sub-channel calibration and equalization portions and/or steps as discussed above and as exemplary illustrated in FIGS. 5A and 5B.

Figure 6A:
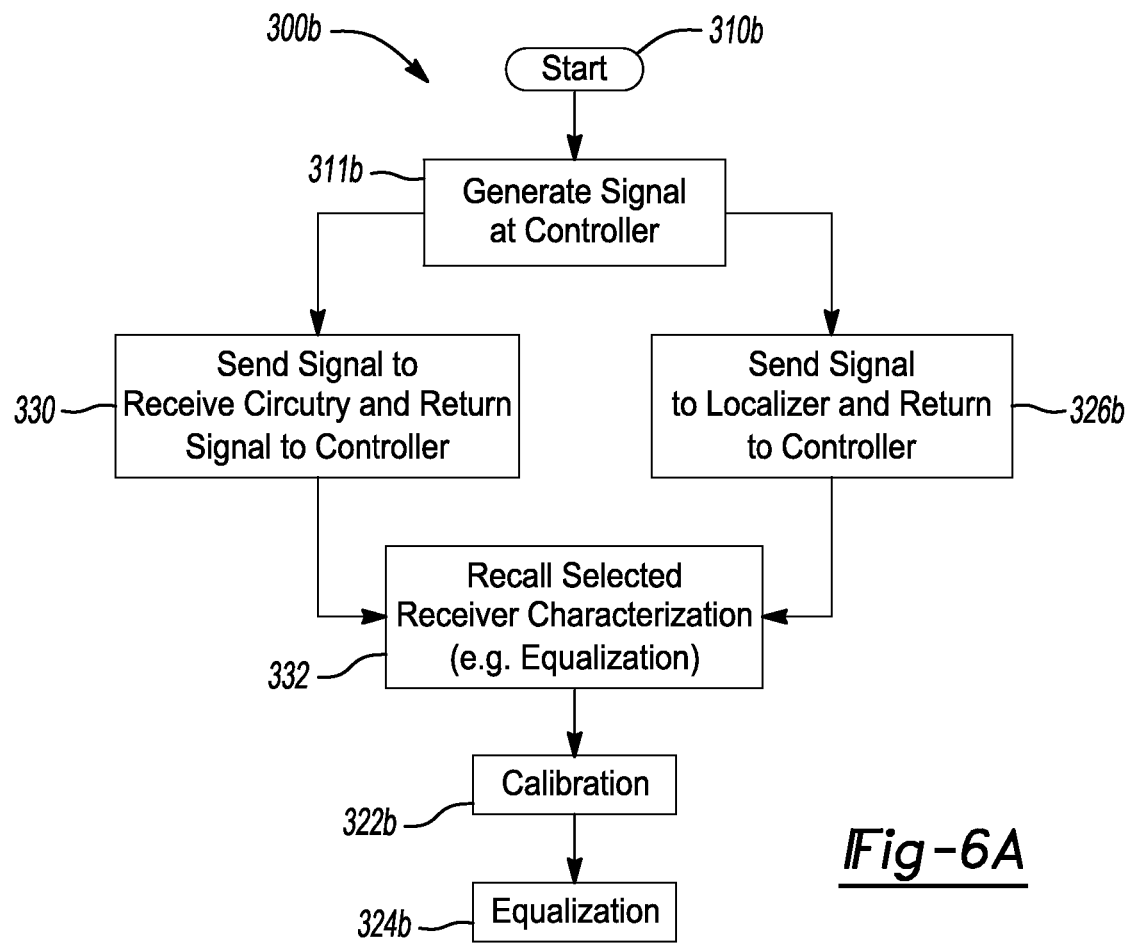
FIG. 6A is a flowchart of a equalization in a spread spectrum navigation system, according to various embodiments.
Figure 6B:
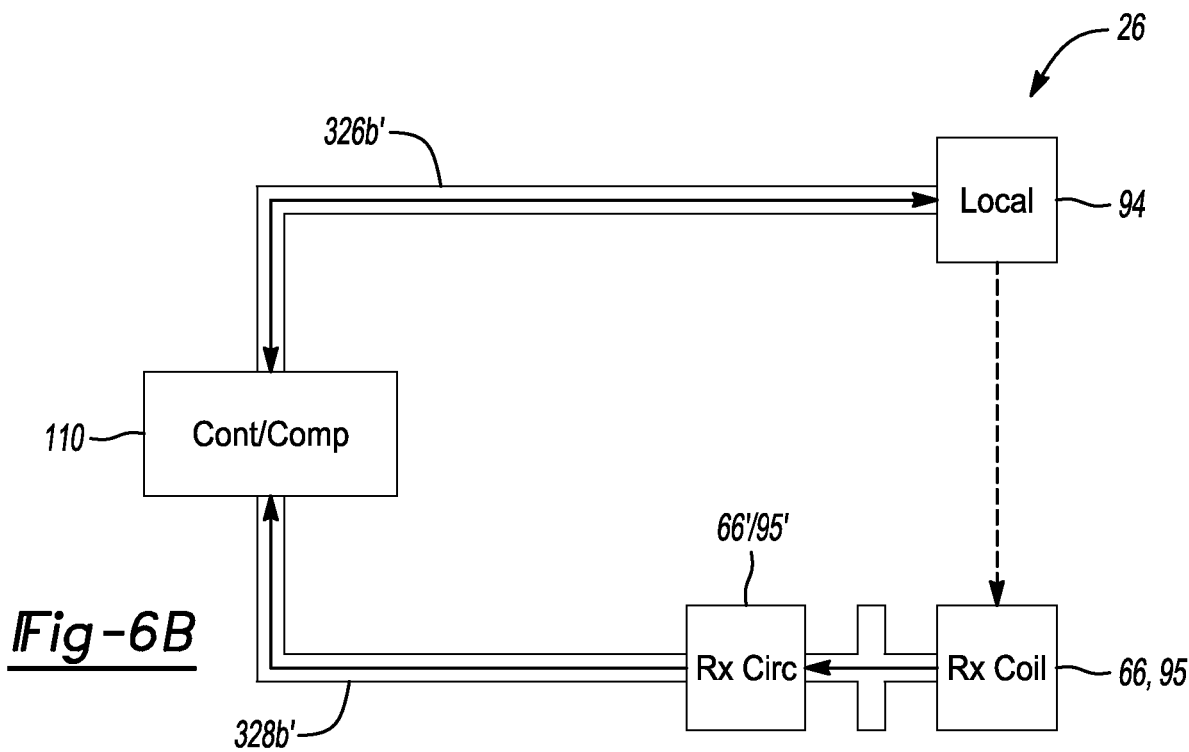
FIG. 6B is a schematic illustration of a navigation system calibration and equalization method of FIG. 6A.

A further and/or alterative sub-channel calibration and equalization may include the method as illustrated in FIGS. 6A and 6B. Initially, a method 300b may include steps or portions that are similar to the method 300 and the method 300a, as discussed above. Like portions will be referenced with like numerals augmented with a "b". Accordingly the method 300b may begin in start block 310b and include generation of a signal at a controller in block 311b. Generation of the signal at the controller may be similar or identical to the generation of the signal at the controller 100 as discussed above.

The signal may be a PN sequence and may then be transmitted or sent to various components of the navigation system 26. For example, the signal may be sent to the localizer 94 through the various components of the localizer system including the circuits, filters, transmitter coils, and the like. The sending of the signal to the localizer 94 in block 326b and the return of the signal to the controller may be similar to that as discussed above in block 326. The signal sent to the localizer 94 may be sent through the various circuitry of the localizer from the controller 110 to the localizer 94. The return signal, that is returned to the controller 110 for various calibration and equalization, as discussed above and further herein, may be returned in various selected manners. As discussed above the signal may be sent or returned to the controller through a various return path from the localizer 94 to the controller 110. In addition or alternatively, various external components may receive the transmitted signal from the localizer 94, such as a magnetometer or the like and the signal from the external components may be returned to the controller. The signal, however, need not be wirelessly transmitted. The signal after having been passed through the various components, such as the circuitry, filter, and coils of the localizer 94, may have a signal that is then returned to the controller 110.

Further, the generated signal may be transmitted to various circuitry and components of the receive 66 channel, as illustrated in FIG. 6B. For example, receive coil circuitry 66'/95' may include various circuitry, cables, filters, and the like that are associated with the tracking device 66 and/or the calibration coil 95. The receive coil circuitry 66'/95' may include various hardware or components that are generally understood to be fixed with the navigation system 26. For example, as discussed above, the controller 110 may be connected to various tracking devices and/or receive tracking device information from various selected tracking devices, such as the tracking device 66. In addition and/or alternatively thereto, the various other tracking devices, such as the tracking device 62 may also be connected to the controller 110.

During a selected procedure, for example, the tracking device coils or components 66, 95 may be interchangeably with the receiver electronics 66'/95' and, therefore, connected to the controller 110. Further, as is understood by one skilled in the art, during a selected procedure or a plurality of procedures, more than one instruments may be individually and separately tracked. Therefore, a plurality of the tracking device 66 may be individually and separately tracked. At a selected time, therefore, the identity of the selected and attached tracking device 66 may be input. The system, such as the controller 110, therefore, may recall from a storage system the characterization of the selected and input tracking device 66. Accordingly the sub-component calibration and equalization of the receiving circuitry 66'/95', may allow for calibration of the navigation system 26 separate from the individual components that are tracked therein, such as with the tracking device 66.

In light of the above, the generated signal from block 311b may be transmitted to the receive circuitry in block 330. The signal received from the receive circuitry 66'/95' may be received in any appropriate manner, such as in a return signal and/or received from external components including a voltage measurement from an external multimeter, or other appropriate sensors.

The calibration and equalization of the navigation system 26, therefore, may also include, therefore, recalling a characterization of a selected receiver, also referred to as a receiver coil or component. For example, as discussed above, various components may be interconnected with the navigation system 26 for navigation of the selected components. Accordingly, the navigation system 26 may be calibrated and equalized without the specific and selected tracking device 66. During a selected time, such as during a procedure, when the specific tracking device is selected, the identity of the selected tracking device may be input (e.g. manually by the user 72, automatically by sensing or receiving a signal from the tracking device, or other appropriate mechanism). The navigation system 26 may recall the previously made and predetermined characterization (including equalization) of the selected tracking device. The characterization of the tracking device, therefore, may have been completed at any prior time. The characterization may include calibration and equalization information may that is previously determined and stored in a selected memory, such as in a database and/or in the memory of the navigation system 26 including the workstation 98 or processor system 98.

The prior determined characterization may be recalled, such as manually and/or automatically and/or combinations thereof, for completing a calibration and an equalization of the entire navigation system 26 including the selected specific receive coil 66/95. Accordingly, when the selected receiver is selected the recalled characterization may be incorporated and/or used with the received signal from the received circuitry in block 330 and the received signal from the localizer in block 326b to allow for calibration and equalization. Thus, with the recalled characterization from block 322, calibration may proceed in block 322b. After calibration in block 322b equalization may occur in block 324b. Calibration and equalization may include such a procedure, as discussed above.

Accordingly, calibration and equalization of the navigation system 26 may occur in an appropriate manner, including those discussed above such as described and illustrated in the FIGS. 4A-6B. It is understood that a calibration and equalization of the navigation system 26 may occur in any appropriate manner and may include any one of the above described systems or methods and/or combinations thereof. For example, an end to end complete calibration and equalization may occur according to the method 300. Further, during a selected procedure, the calibration method 300b may be used to augment and/or update a calibration equalization of the navigation system 26 when the tracking device is added and/or changed during a selected procedure and/or between procedures. Accordingly, it is understood that the calibration and equalization may occur in any appropriate manner and need not be limited to only a single one of the methods as discussed above, but may include a plurality and/or combination thereof, such as an end to end calibration and equalization according to the method 300 that may be supplemented and/or redone according to the sub-channel procedures according to either and/or both of the method 300a and 300b.

Figure 7:
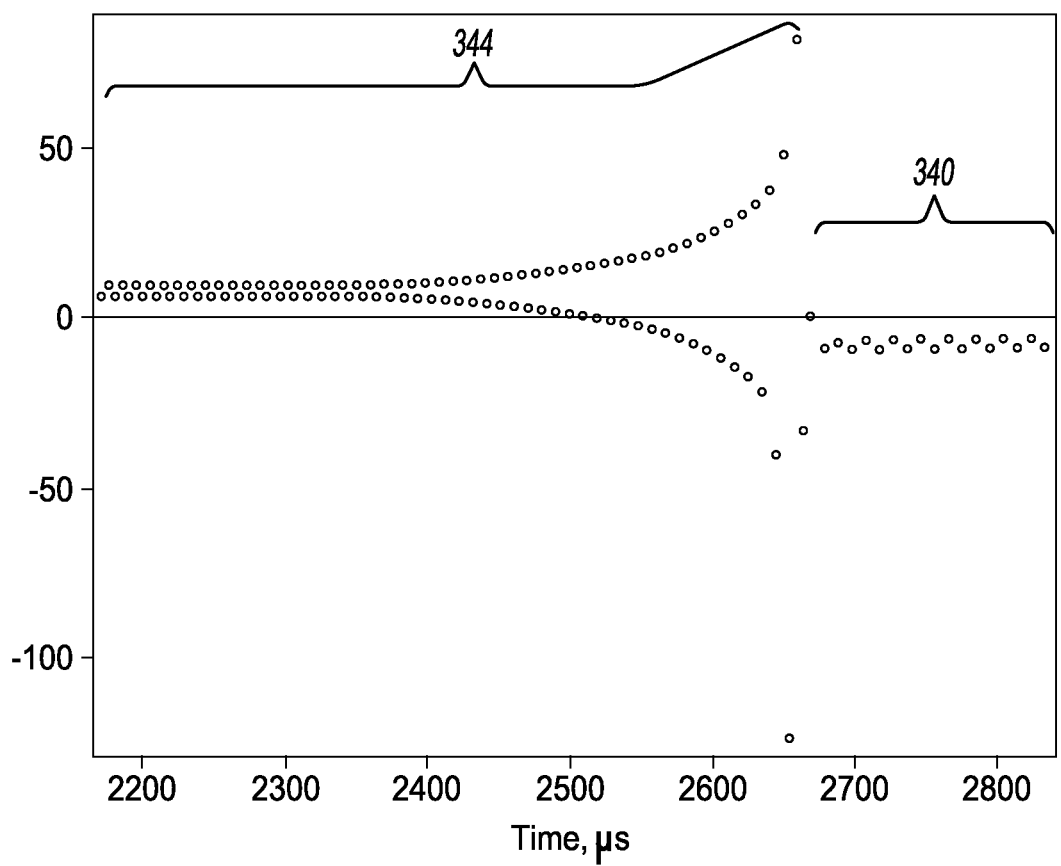
FIG. 7 is a graph on a magnitude response of a non-equalized received navigation signal, according to various embodiments.

According to various embodiments, including those discussed above, the signal received at the tracking device 66 may be equalized with the equalizer 190 in step 324 according to the equalization process discussed above. With reference to FIG. 7, a non-equalized impulse response may include a causal portion 340 and anti-causal portion 344. The anti-causal portion may be used to compensate for various components of the navigation system 26 and may vary in light thereof. Accordingly, various different components may be used in the navigation system 26 and allow or cause the causal portion 340 to vary. The causal portion 340 may be used to compensate for variation and phase in the system's pass band and also in various components of the circuitry of the localizer 94. The equalized signal in block 324, therefore, may use the pre-equalization impulse response as illustrated in FIG. 7 to calibrate and equalize the signal.

The localizer 94 may transmit a signal to generate an electromagnetic field. The signal may be a spread spectrum signal that is transmitted with a BNO scheme. The signal, including the BNO scheme, may be referred to as a tracking signal that includes an binary signal. The binary signal may be measured at the tracking device 66 that relates to the transmitted signal. The received signal may include various components, as discussed further herein, due to various distortions as discussed above and also herein. The equalization may assist in ensuring the recovery of the impulse response transmitted by the localizer 94.

Figure 8:
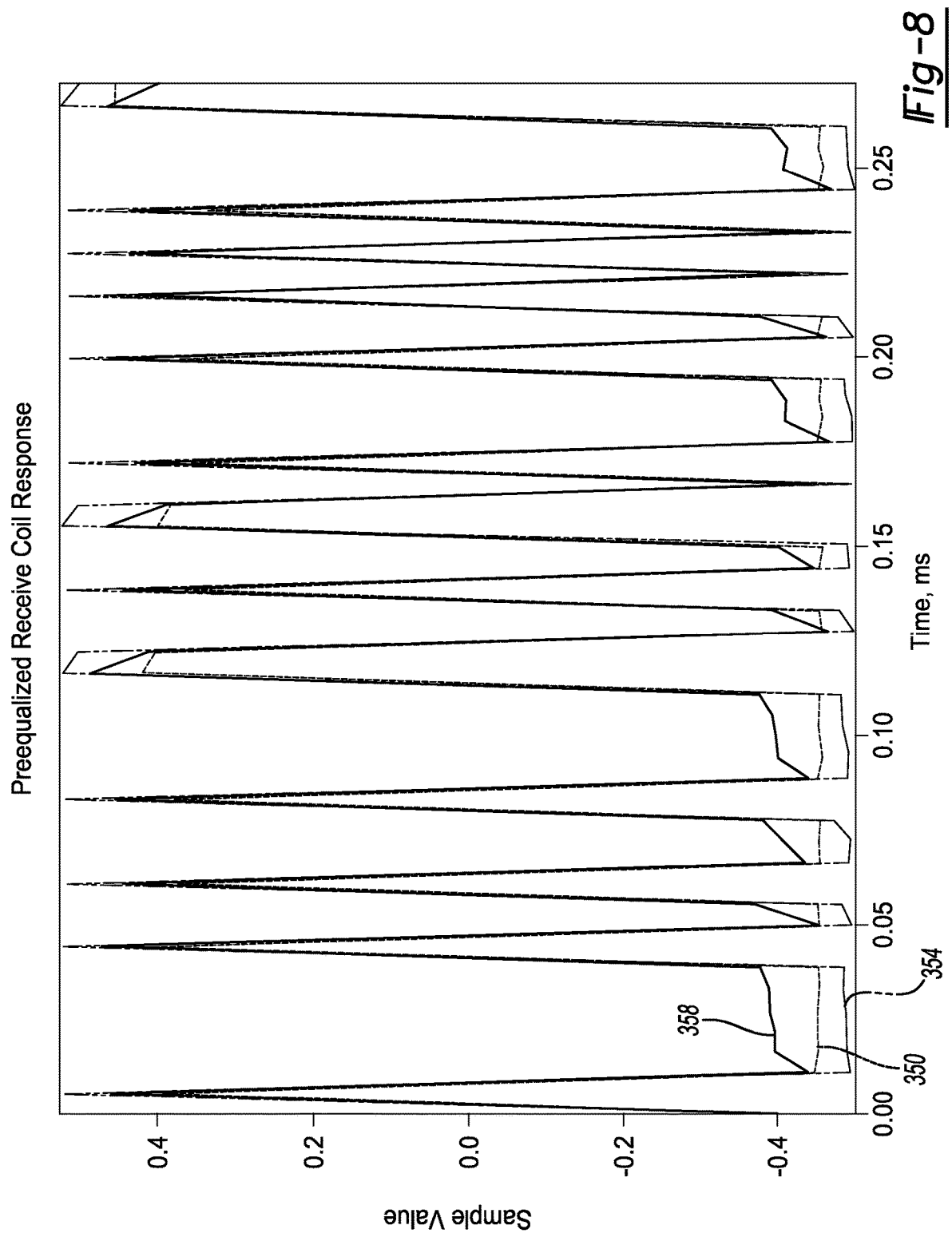
FIG. 8 is a graph of a magnitude response of a non-equalized received navigation signal with and without distorting items, according to various embodiments.
Figure 9:
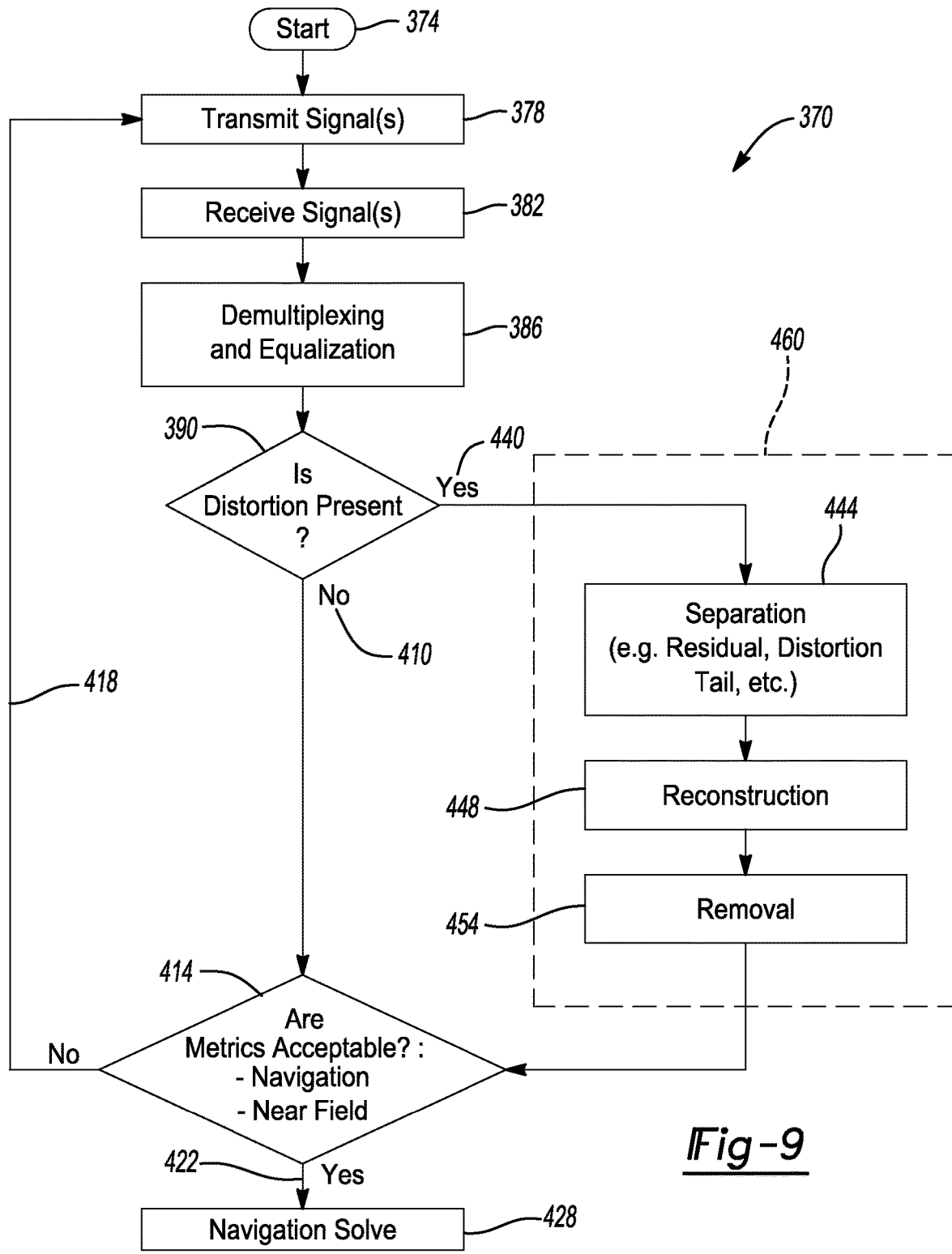
FIG. 9 is a flowchart of a code-multiplexed spread spectrum navigation system with distortion detection and correction, according to various embodiments.

Turning reference to FIG. 8 and FIG. 9, a pre-equalized signal is illustrated in FIG. 8 as received by the tracking device 66. The pre-equalized signal in FIG. 8 illustrates different received signals due to system distortions and including distortion causing materials in the field or near the path of the tracking device 66. For example, graph line 350 relates to a value over time of the pre-equalized signal received by the tracking device 66 with no distorting item. A second graph line 354 illustrates the received signal over time when a portion of aluminum is placed or located near or causes distortion in the received signal. A third graph line 358 illustrates the received signal when a selected steel material is located near the tracking device 66. As illustrated in FIG. 8, by the graph lines 350-358, the signal received by the tracking device 66 may vary depending upon material located near the tracking device 66 and/or that would distort the signal transmitted by the localizer 94. As discussed further herein, the distortion caused by selected materials may be removed by analyzing the received signal to determine whether distortion is present and, if present remove the same. As discussed herein, distortion, whether present or not, may be determined. If distortion is determined to be present, it may be removed to allow recovery of an undistorted tracking signal including the impulse response.

With reference to FIG. 9, a method or process of navigation 370 is illustrated. The navigation process can begin at start block 374 and include transmitting a signal or signals in block 378. As discussed above the signal as transmitted may include the spread spectrum signal according to the BNO scheme, discussed above. The signal transmitted by the localizer 94 may be transmitted into the navigation volume 180. As discussed above, the transmitted signal may generate near field magnetic fields with wavelengths greater than or equal to 10 meters. The navigation volume 180 may be dependent upon various factors such as the size of the coil 200, the overall size of the localizer 94, power transmission, and other factors. Nevertheless the navigation volume 180 may be a volume of about 0.001 m$^3$ to about 1 m$^3$, including about 0.01 m$^3$ to about 0.5 m$^3$.

The transmitted signal or signals may be received by the tracking device 66 in block 382. The received signal in block 382 may be received by the tracking device 66 and/or transmitted to the navigation processor 102. It is understood that the method or process 370 may be executed by the processor 102 with a transmit signal 378 may be a signal to the localizer 94 to transmit a signal and may receive signal in block 382 may be the signal received and transmitted to the navigation processor 102 from the tracking device 66. The method 370 may include a transmission of the signal by the localizer 94 and receiving the signal by the tracking device 66, or vice versa, and the navigation processor 102 may execute instructions to make a determination of the navigation in the method 370.

After the signal or signals is received in block 382, a signal may be processed, such as demultiplexed and equalized, in block 386. As discussed above, the received signal is received with the BNO scheme and therefore each cyclically shifted or offset code, corresponding to each transmit coil, may be demultiplexed from the received signal for further analysis. Equalization in block 386 may be similar to the equalization block 324, as discussed above. Generally, as discussed above, the localizer 94 may include the coil 200a and the tracking device 66 may include the coil 66a. It is understood that discussion herein to the coil 66a may include or be similar to the discussion of a plurality of coils at the tracking device 66 and discussion of the single coils 66a herein is merely exemplary. The equalization between the coil 66a and the coil 200a may allow for the impulse response recovery of the transmitted signal.

Figure 10:
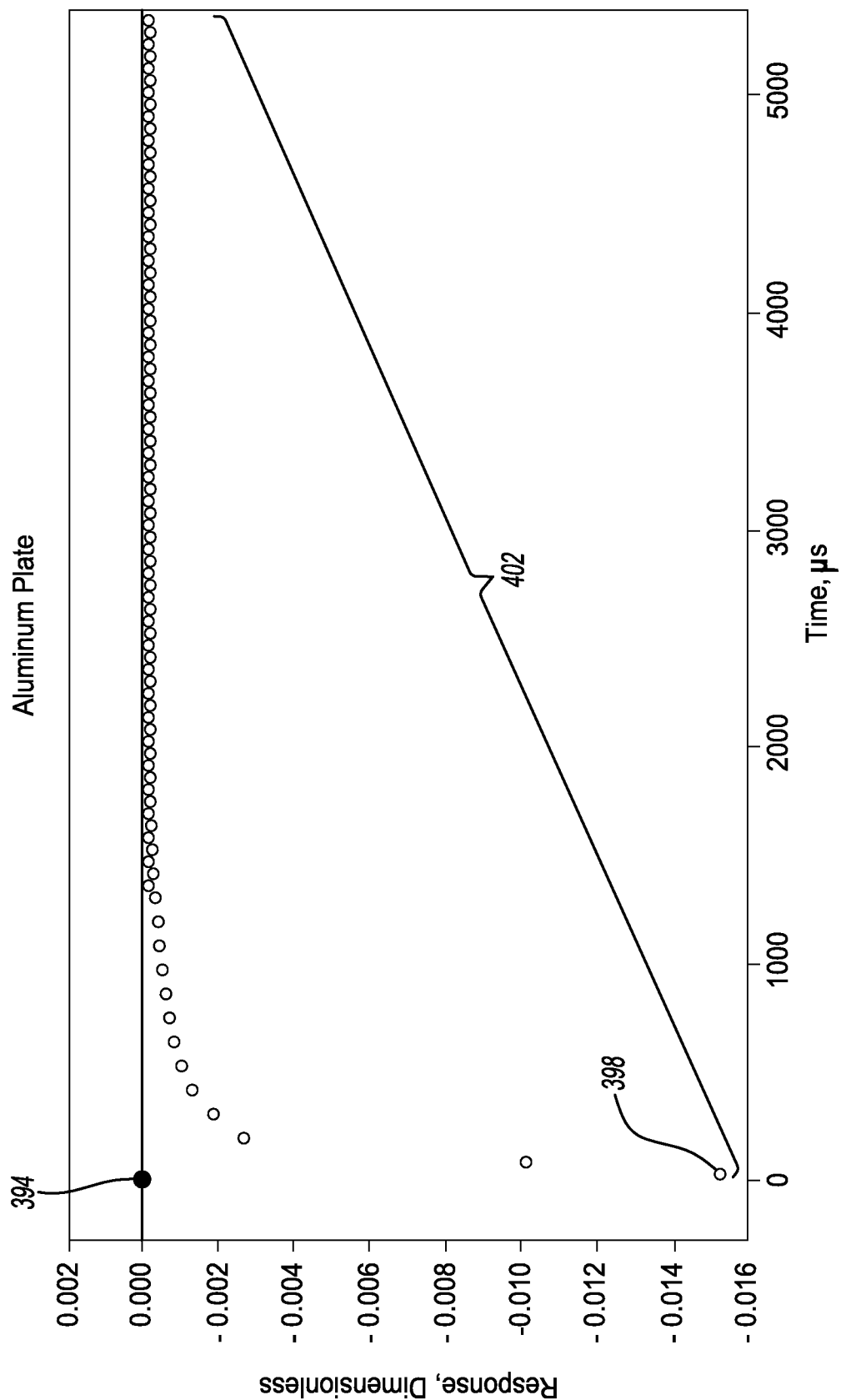
FIG. 10 is a graph of a magnitude response of an equalized received navigation signal with distorting items present, according to various embodiments.

After equalizing the signal in block 386, as discussed above such as with the equalizer 190, the equalized signal may be evaluated to allow for a determination in block 390 of whether distortion is present. The determination of whether distortion is present may be made based upon the received signal, for example as illustrated in FIG. 10. The received signal, as illustrated in FIG. 10, may include a determination or evaluation of an initial impulse as illustrated by a black dot 394 in the graph of FIG. 10. The impulse response may be the equalized impulse response from the received signal as equalized in block 386. The impulse response may further include a residual or tail that is a non-impulse or distortion portion that may include one or more tail signals or points 398. The tail points 398 may include a plurality of tail points in a tail portion 402. The tail portion 402, or a presence of a tail portion, may be used to determine whether distortion is present. Accordingly, if the signal, that includes an impulse response as illustrated in FIG. 10, as graphed over time, includes substantially no tail, a determination that no distortion is made, and a no-distortion path 410 is followed. Calibration and equalization, as discussed above according to one or more of the various methods, may include a characterization of the system including a noise floor and a distortion limit. No presence of tails, i.e. distortion, may be defined as within these previously determined limits.

If no distortion is found in the received signal after the equalization, such as determining that the tail 402 is not present in the signal, and the No distortion path 410 is followed, then a navigation of the tracking device 66 may be performed without correcting for a distortion. As discussed above, distortion may be present or found in the received signal due to various distorting items in the signal path, such as effecting the signal transmitted by the localizer 94. Distortion may be caused by various items such as items in or near the navigation system 26, as discussed above including the imaging device 80, the instrument 68, the operating or patient support table 104, or other items. Further, distortion may occur due to other items actively transmitting a field, such as an electrical field from an electrically powered drill, other coils in the localizer 94 other than the pair being resolved or evaluated at a time, or other items. The equalization may be made on a pairwise (e.g. single coil 200a of the localizer 94 and single coil 66a and the tracking device 66) basis. Accordingly, a determined pose of the tracking device 66 may be made by determining a pose of each of the coils 66a-66c and the tracking device 66 for each of the coils 200a-200n of the localizer 94. It is understood, however, that tracking of the instrument 68 with the tracking device 66 may include navigation between a selecting number of coils of the localizer and the tracking device 66. Thus, for example, navigation may occur with one tracking device and using nine or twelve transmit coils in the localizer 94. Other examples may include combinations of one receive coil using five transmit coils to three receive coils using three transmit coils to twelve receive coils using one transmit coil.

After determining there is no distortion, an evaluation of whether certain metrics are accepted may be made in block 414. Metrics may include signal metrics, or any other appropriate metrics. Further predetermined acceptable ranges or thresholds for the metrics may be made and saved to be accessed by the navigation processor 102. In various examples, predetermined signal strength values that are above or below a threshold may be determined. Thus, if a signal received is above a threshold it may be determined that a tracking device is too near the localizer and if a signal received is below a threshold the tracking device may be too far from the localizer. The threshold, however, may relate to localizer size and/or power, tracking device configuration, etc. Accordingly the metrics may be analyzed and determined in block 414.

If it is determined that the metrics are not acceptable in block 414, a return or loop path 418 may be followed to transmit the signal in block 378 and/or to the receive signal again in block 382. In various embodiments, the transmission may repeat automatically, thus looping to transmission may not be necessary or desirable and looping to receiving in block 382 may be appropriate. By receiving the signal again at the tracking device 66, the signal may be reanalyzed. The transmitted signal may be transmitted over a selected span of time such as milliseconds, including a sequence of 1 to 100 milliseconds including about 30 milliseconds that may or may not be followed by a break or pause in a transmission. Therefore, the determination of whether the metrics are acceptable in block 414, if not found to be acceptable, may allow for receiving a signal again in block 382 but not distributing navigation of the navigation system 26 in a time acceptable by the user 72. However, if the metrics are not found to be acceptable over a reasonable period of time, such as about 30 to 500 milliseconds, the navigation system 26 may provide an output, such as with the display device 84 that may identify to the user 72 that an error has occurred and must be resolved.

If the metrics are acceptable in block 414 a YES or solve path 422 may be followed. The solve path 422 may lead to a navigation solve or pose determination in block 428. The navigation solve in block 428 may allow for illustration of the representation 68i on the display device relative to the image data 108 on the display device 84. The navigation solve allows for illustration and/or determination of a pose of the tracking device 66 relative to the subject 30. Thus, navigation may occur of the instrument 68 relative to the subject 30.

With continuing reference to FIG. 9, the navigation method 370 may also follow a distortion determined or distortion found path 440, if distortion is found to be present in block 390. The Yes distortion path 440 may lead to or enter a distortion correction, also referred to as remove, subroutine 460. The subroutine 460 may include various procedures or processes to identify and correct for selected distortion, as discussed herein. In the subroutine, it is understood by one skilled in the art, that the herein described processes may be carried out sequentially and/or simultaneously, as discussed herein. Accordingly, while FIG. 9 illustrates that the subroutine in a selected order, the processes in the subroutine 460 may occur substantially simultaneously.

The cause of distortion may be any cause of distortion, including those discussed above. For example, a metal object that is conductive may be in the path of the field generated by the localizer 94. For example, as illustrated in FIG. 1, an aluminum object, such as the tray 71 that may be formed therefrom, may be in the path of the signal from the localizer 94 to the tracking device 66. The aluminum tray 71 may cause the tail 402, as illustrated in FIG. 10. The tail 402 may include a plurality of response data points separated by time as illustrated along the x-axis in FIG. 10. As exemplary illustrated in FIG. 10 the time may be separated by increments of microseconds but may also be any appropriate time segmentation. Nevertheless, the determination and identification of the tail 402 may be used to ensure or determine an appropriate magnitude of the initial impulse 394.

Generally, the initial impulse 394 occurs at a time "zero" when receiving the signal in block 382. In particular, the signal is transmitted in block 378 and received in block 382 and the receiving of the signal in block 382 would be time zero which is also understood to be the start of the PN code or signal or shifts of the PN code. Any trailing or residual signal received signal thereafter may be caused due to distortion or a distorting object within the field along the signal path, such as the tray 71. Thus, the initial impulse 394 may be distorted, such as in magnitude, and this distortion noted by the distortion tail 402.

With continuing reference to FIG. 10 the initial impulse 394, may be illustrated on a graph for ease of discussion and calculation, as discussed herein. The initial impulse 394 is illustrated at zero time response to exemplary illustrate the initial impulse at time zero on the X-axis. Further, the initial impulse is shown at zero magnitude to better illustrate the value of the residual or tail response received in block 382 if distortion is present. The corrected or non-distorted dimension of the initial impulse 394 may be determined by calculating the tail 402 into the initial impulse 394. The initial impulse and the tail may generally be a causal response where the tail 402 may be used to determine the expected or un-distorted impulse magnitude.

The distortion present path 440 may first go to a residual or tail separation in block 444. The residual separation may include a determination of all of the tail portion. As discussed above, the initial impulse at time zero may be determined such as based upon a determined or selected amount of time between the transmit signal and the received signal in block 378, 382 respectively. For example, it may be determined that the time between the transmitting of the signal from the localizer 94 and the receiving of the signal at the tracking device 66 may be much less than microseconds. Accordingly, the navigation system 26 may determine that a received signal at the selected amount of time after transmission of the signal in block 378, may be a zero time and the initial impulse. Any recovered impulse response thereafter may be determined to be the tail 402. The determination of the tail 402, however, may be in any appropriate manner, such as any recovered signal after the identified initial impulse. Regardless, the tail 402, that may be determined or detected in block 390 when determining whether a distortion is present, may be separated from the initial impulse or first impulse 394. The separation of the residuals provides separation of the tail dimensions or magnitude for further reconstruction.

After separation of the tail in block 444, a reconstruction may be performed in block 448. The reconstruction block 448 may include reconstruction the distortion impulse response. As discussed above, the initial or zero time impulse 394 may be distorted and this distortion may be determined by the tail 402, if present. Accordingly, once the tail is separated in block 444 the separated tail may be reconstructed into the distortion initial impulse to determine an actual or corrected impulse. The reconstruction may be in any appropriate type of reconstruction.

For example a direct reconstruction may include an addition or additive reconstruction by adding the values of the tail 402 for a selected amount of time, such as about 1 to 10 milliseconds including 5 milliseconds, to the value of the distortion initial or zero time impulse. The direct reconstruction may allow for a fast reconstruction of the distortion impulse and may be appropriate for selected materials, such as conductive materials such as certain plastics or polymers, metal alloys or the like.

Reconstruction may also include a modeled reconstruction of the impulse response that may be based upon weighting certain portions of the tail, adding or eliminating certain portions of the tail 402, or other appropriate modeling techniques. In various embodiments, the reconstruction may not include first removing the tail in block 444, but may include simultaneous separation and modeling. IN various embodiments, the tail may be summed and added to the impulse, particularly for conductive distortion materials. In other words, as a function of the residuals in a direct calculation summing the residuals to determine the distortion initial impulse. In a modeled or indirect calculation, the tail may be decomposed into separate functions and then fit for determining the distortion effect. For example, the decomposed functions may be fit to pre-determined or measured distorting materials or items. In other words, residuals may be modeled with a combination of parameterized impulse responses having conductive and conductive and magnetic contributions and/or with a combination of measured impulse responses including expected conductive and conductive and magnetic contributions.

The reconstruction may be made in block 448 to determine the corrected or undistorted impulse response in block 454. Following the reconstruction of the distortion impulse response in block 448, a removal or deconvolution of the impulse response is made in block 454. The removal or deconvolution of the impulse response in block 454 may include separating the distortion impulse response from the full impulse response via removal or deconvolution to determine the corrected or undistorted impulse response and impulse.

Following the removal or deconvolution in block 454, the navigation method 370 may then enter the determination of whether selected metrics are acceptable in block 414. Similar to that discussed above, the determination of whether the metrics are acceptable in block 414 may allow for receiving an additional signal in the loop path 418 and/or navigation solving in block 428.

Accordingly, the method 370 may follow a no distortion path 410 and/or a distortion path 440 to solve a navigation and determine the pose of the tracking device 66 in space relative to the subject 30. The method 370 may include the no-distortion path 410 and the distortion path 440, the distortion path may include the distortion correction subroutine 460. The distortion correction subroutine 460 may be executed by the controller 110 or navigation processor 102 to allow for removal or correction of the distortion from a distorting object to determine a true or correct pose of the tracking device 66. The distortion may be detected in block 390 and removed in the distortion correction subroutine 460 as discussed above.

As briefly discussed above, the subroutine 460 may be substantially sequential as discussed above. Thus, the various calculations may be processed, such as with a processor executed instructions, in the order as discussed above and illustrated directly in FIG. 9. In various embodiments, however, all of the processes in the subroutine 460 may occur simultaneously or selected plurality of the processes may occur simultaneously. In other words, the subroutine 460 may occur via concurrent separation 444, reconstruction 448, and removal or deconvolution 454. The subroutine 460 may, however, still follow the decision of wherein the recovered impulse response includes a distortion tail in block 390. Then, the subroutine 460 may include simultaneous separation and deconvolution of reconstructed distortion impulse responses from the recovered impulse response to find a corrected impulse response and impulse. The corrected impulse response and impulse may be determined with a fit of the residuals to a combination of measured or modeled impulse responses including expected conductive and conductive and magnetic contributions.

Accordingly, the navigation system 26, as discussed above, may be used to determine a pose of the tracking device 66 that is associated, such as connected to, the instrument 68. The navigation system 26 may therefore track the tracking device 66 and navigate the instrument 68 such as by illustrating the instrument 68 as the representation 68i on the display device 84. The use of the spread spectrum transmission may allow for a low power and high fidelity signal transmission with select electronics, such as the "H" bridge configuration discussed above. Further a selected scheme, such as the BNO scheme, may allow for transmission of a signal based substantially free of distortion or confusion with extraneous signals relative to the tracking device 66. Further the received signal may be analyzed or reconstructed to determine is distortion is present or has been caused by distorting object and, if present, may be removed. Thus the pose of the tracking device 66 may be determined with a selected preciseness and correctness due to the received signal at the tracking device 66.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of operating a navigation system configured to navigate an instrument during a procedure, the method comprising:
generating a signal with a controller, wherein the signal is a spread spectrum signal including a binary pseudo noise signal;
sending the signal to a transmitter system;
transmitting the signal with the transmitter system;
receiving the transmitted signal at a receiver;
sending a receiver signal to the controller based on the transmitted signal that was received at the receiver;
evaluating the receiver signal to characterize and determine how to account for a hardware noise in the transmitter system and receiver of the navigation system;
wherein evaluating the receiver signal to characterize and account for the hardware noise includes calibrating and equalizing the receiver signal with the signal from the controller to generate an equalized signal by removing distortions of the controller and the receiver;
wherein the equalized signal is used to determine a pose of a tracking device with a tracking device signal and noise from external distortion.

2. The method of claim 1, wherein sending the signal to the transmitter system includes sending the signal from the controller to the transmitter system via a wired connection.

3. The method of claim 1, further comprising:
sending the signal through at least one coil and one electronic component of the transmitter system prior to transmitting the signal.

4. The method of claim 3, further comprising:
sensing the signal with a coil of the receiver; and
sending the sensed signal through at least one receiver electronic component prior to sending the receiver signal to the controller.

5. The method of claim 1, further comprising:
generating a tracking signal in a spread spectrum with the controller;
transmitting the tracking signal;
sensing the tracking signal with the tracking device; and
evaluating the sensed tracking signal with the controller to determine the pose of the tracking device based on the characterization of the navigation system.

6. The method of claim 1, further comprising:
providing at least one of the (i) transmitter system to include a plurality of transmitter coils or (ii) the receiver to include a plurality of receiver coils;
wherein evaluating the receiver signal to characterize and account for the hardware noise includes receiving the receiver signal from each transmitter coil of each of the plurality of transmitter coils or each of the receiver coils of the plurality of receiver coils.

7. A method of operating a navigation system configured to navigate an instrument during a procedure, the method comprising:
generating a first signal with a controller;
sending the first signal to a transmitter system;
receiving at the controller a transmitter signal from the transmitter system based on the first signal sent to the transmitter system;
generating a second signal with the controller;
sending the second signal to a receiver system;
wherein at least one of the generated first signal or the generated second signal is a spread spectrum signal including a binary pseudo noise signal;
receiving at the controller a receiver signal from the receiver system based on the second signal sent to the receiver system;
evaluating the transmitter signal and the receiver signal to characterize the navigation system; and
generating an equalized signal based on the evaluation of the transmitter signal and the receiver signal to characterize the navigation system including calibrating and equalizing the transmitter signal and the receiver signal to the respective first signal and the second signal to account for hardware noise in the transmitter system and the receiver system;
wherein the equalized signal is operable to be used to determine a pose of a tracking device by removing distortions of the controller and the receiver and having a tracking device signal and noise from external distortion.

8. The method of claim 7, further comprising:
sending the first signal through at least one coil and one electronic component of the transmitter system prior to receiving at the controller the transmitter signal.

9. The method of claim 8, further comprising:
sending the second signal through at least one coil and one electronic component of the receiver system prior to receiving at the controller the receiver signal.

10. The method of claim 9, further comprising:
generating a tracking signal in a spread spectrum with the controller;
transmitting the tracking signal;
sensing the tracking signal with the tracking device; and
evaluating the sensed tracking signal from the characterized navigation system with the controller to determine the pose of the tracking device based on the characterization of the navigation system.

11. The method of claim 10, wherein the first signal and the second signal are the same signal.

12. A method of operating a navigation system configured to navigate an instrument during a procedure, the method comprising:
generating a first signal with a controller;
sending the first signal to a transmitter system;
receiving at the controller a transmitter signal from the transmitter system based on the first signal sent to the transmitter system;
generating a second signal with the controller;
sending the second signal to a first portion of a receiver system;
wherein at least one of the generated first signal or the generated second signal is a spread spectrum signal including a binary pseudo noise signal;
receiving at the controller a receiver signal from the receiver system based on the second signal sent to the first portion of the receiver system;
recalling a receiver characterization of a second portion of the receiver system; and
evaluating the transmitter signal, the receiver signal, and the recalled receiver characterization to characterize the navigation system;
wherein evaluating the transmitter signal, the receiver signal, and the recalled receiver characterization includes calibrating and equalizing the transmitter signal and the receiver signal to the respective first signal and the second signal to account for hardware noise in the transmitter system and the receiver system to generate an equalized signal;
wherein the equalized signal is used to determine a pose of a tracking device by removing distortions of the controller and the receiver and having a tracking device signal and noise from external distortion.

13. The method of claim 12, wherein the first signal and the second signal are the same signal.

14. The method of claim 12, further comprising:
sending the first signal through at least one coil and one electronic component of the transmitter system prior to receiving at the controller the transmitter signal.

15. The method of claim 14, wherein the second portion of the receiver system includes the tracking device, the method further comprising:
receiving an identification of the tracking device;
wherein recalling the receiver characterization of the second portion of the receiver system includes accessing a database of a predetermined characterization of the tracking device including at least one of calibration based upon various parameters.

16. The method of claim 15, further comprising:
generating a tracking signal in a spread spectrum with the controller;
transmitting the tracking signal;
sensing the tracking signal with the tracking device; and
evaluating the sensed tracking signal with the controller to determine the pose of the tracking device based on the characterization of the navigation system.

* * * * *